US007799934B2

(12) United States Patent  (10) Patent No.: US 7,799,934 B2
Antilla et al.  (45) Date of Patent: Sep. 21, 2010

(54) ENANTIOSELECTIVE RING-OPENING OF AZIRIDINES

(75) Inventors: Jon C. Antilla, Tampa, FL (US); Emily B. Rowland, Tampa, FL (US); Gerald B. Rowland, Tampa, FL (US)

(73) Assignee: University of South Florida, Tampa, FL (US)

( * ) Notice: Subject to any disclaimer, the term of this patent is extended or adjusted under 35 U.S.C. 154(b) by 260 days.

(21) Appl. No.: 12/215,837

(22) Filed: Jun. 30, 2008

(65) Prior Publication Data

US 2009/0030212 A1  Jan. 29, 2009

Related U.S. Application Data

(60) Provisional application No. 60/947,019, filed on Jun. 29, 2007.

(51) Int. Cl.
C07D 203/04 (2006.01)
(52) U.S. Cl. .................................................. 548/954
(58) Field of Classification Search ................. 548/954
See application file for complete search history.

(56) References Cited

U.S. PATENT DOCUMENTS

| 6,258,960 B1 | 7/2001 | Antilla et al. |
| 6,307,087 B1 | 10/2001 | Buchwald et al. |
| 7,038,073 B2 | 5/2006 | Chorghade et al. |
| 2004/0198999 A1 | 10/2004 | Choudary et al. |
| 2006/0142586 A1 | 6/2006 | Chorghade et al. |

FOREIGN PATENT DOCUMENTS

WO  WO 2005/095347  *  3/2005

OTHER PUBLICATIONS

X. Eric Hu (Tetrahedron 60 (2004) 2701-2743).*
Coull et al. (Synthesis 2000, No. 10, 1347-1365).*
Sommerdijk et al. (J. Org.Chem. 1997, 62, 4955-4960).*
Akiyama et al. (Angew. Chem. Int. Ed. 2004, 43, 1566-1568.*
Uraguchi et al. (J. Am. Chem. Soc. 2005, 127, 9360-9361).*
Antilla et al. (J. Am. Chem. Soc. 1999, 121, 5099-5100; provided by Applicants).*
International Search Report, PCT/US2008/008130, dated Feb. 3, 2009, 3 pages.
Fukuta et al., J. Am. Chem. Soc. 2006, 6312-6313, 128 (19).
Green, T. Protective Groups in Organic Synthesis, 1991, Chapter 7, pp. 315-385, John Wiley and Sons, Inc.
Huang et al., Nature 2003, 146, vol. 424.
Jacobson et al., Organic Letters 1999, 1611-1613, 1.
Li et al., Organic Letters 2007, 4065-4068, 9 (20).
Liang et al., Chem. Comm. 2007, 4477-4479.
Pochlauer et al., Helv. Chem. Acta. 1984, 1238, vol. 67.
Akiyama et al., Angew. Chem. Int. Ed. 2004, 43, 1566.
Anderson and Milowsky, J. Med. Chem. 1986, 29, 2241.
Antilla and Wulff, Angew. Chem. Int. Ed. Engl. 2000, 39, 4518.
Antilla and Wulff, J. Am. Chem. Soc. 1999, 121, 5099.
Bao et al., J. Am. Chem. Soc. 1996, 118, 3392.
Chandrasekhar et al., "An efficient method for opening nonactivated aziridines with TMS azide." Tetrahedron. 2000, 41, 10079.
Ekegren et al., Org. Biomol. Chem. 2003, 1, 358.
Fanta and Walsh, J. Org. Chem. 1966, 31, 59.
Fukuta et al., "De novo synthesis of Tamiflu via a catalytic asymmetric ring-opening of meso-aziridines with TMSN3." J. Am. Chem. Soc. 2005, 127, 6312.
Heller et al., J. Am. Chem. Soc. 1997, 119, 10551.
Hu, X.E., "Nucleophilic ring opening of aziridines." Tetrahedron. 2004, 60, 2701-2743.
Kang et al., J. Am. Chem. Soc. 2007, 129, 1484.
Li Z., "Enantioselective ring opening of meso aziridines catalyzed by tridentate Schiff base chromium (III) complexes." Organic Letters. 1999, 1(10), 1611-1613.
List et al., J. Am. Chem. Soc. 2000, 122, 2395.
Lucet et al., "The chemistry of vicinal diamines." Angew. Chem. Int. Ed. 1998, 37, 2580-2627.
Marquis et al., J. Med. Chem, 2001, 44, 725.
Matsubara et al., "Yb(CN)3-catalyzed reaction of aziridines with cyanotrimethylsilane. A facile synthesis of optically pure beta-amino nitriles." Tetrahedron Letters. 1990, 31, 6379.
McCoull and Davis, "Recent synthetic applications of chiral aziridines." Synthesis. 2000, 10, 1347-1365.
Minakata et al., "Lewis Base catalyzed ring opening of aziridines with silylated nucleophiles." Org. Lett. 2005, 7, 3509.
Mita et al., "Catalytic enantioselective desymmetrization of meso-N-acylaziridines with TMSCN." J. Am. Chem. Soc. 2005, 127, 11252.
Mita et al., "Second generation catalytic asymmetric synthesis of Tamiflu: Allylic substitution route." Organic Letters. 2007, 9(2), 259-262.
Mordini et al., Tetrahedron. 2002, 58, 7153.
Nugent et al., J. Am. Chem. Soc. 2004, 126, 3418.
Osborn and Sweeny. "The asymmetric synthesis of aziridines." Tetrahedron: Asymmetry. 1997, 8, 1693.
Paras and MacMillan, J. Am. Chem. Soc. 2001, 123, 4370.
Rowland et al., J. Am. Chem. Soc. 2005, 127, 15696.
Rowland et al., Org. Lett. 2007, 9, 2609.
Sabitha G. "Cerium(III) chloride promoted highly regioselective ring opening of epoxides and aziridines using NaN3 in acetonitrile." Org. Let. 2002, 4, 343.
Sigman et al., Angew. Chem. Int. Ed. 2000, 39, 1279.
Tanner D. "Chiral aziridines—Their synthesis and use in stereoselective transformations." Angew. Chem. Int. Ed. Engl. 1994, 33, 599.
Terada et al., J. Am. Chem. Soc. 2007, 129, 292.
Uraguchi and Terada, J. Am. Chem. Soc. 2004, 126, 5356.
Uraguchi et al., J. Am. Chem. Soc. 2004, 126, 11804.
Uraguchi et al., J. Am. Chem. Soc. 2005, 127, 9360.
Wang et al., J. Am. Chem. Soc. 2006, 128, 8156.
Wu et al., "N-Heterocyclic carbene: a highly efficient catalyst in the reactions of aziridines with silylated nucleophiles." Tetrahedron Lett. 2006, 47, 4813.
Wu et al., "Ring opening of aziridines with silylated nucleophiles under neutral conditions." Eur. J. Org. Chem. 2005, 4760.
Wu et al., "DABCO: An efficient organocatalyst in the ring-opening reactions of aziridines with amines or thiols." Eur. J. Org. Chem. 2005, 4271-4275.
Xue et al., Angew. Chem. Int. Ed. Engl. 2001, 40, 2271.
Zhang et al., Helv. Chem. Acta. 1993, 76, 2602.

* cited by examiner

*Primary Examiner*—Kamal A Saeed
*Assistant Examiner*—Valerie Rodriguez-Garcia
(74) *Attorney, Agent, or Firm*—Bryan Cave LLP

(57) ABSTRACT

A process for the preparation of a nucleophilic addition product of an aziridine and a nucleophile, the process comprising treating the arizidine with the nucleophile in the presence of a biaryl phosphoric acid catalyst.

20 Claims, No Drawings

ENANTIOSELECTIVE RING-OPENING OF AZIRIDINES

CROSS-REFERENCE TO RELATED APPLICATIONS

This application claims the benefit of U.S. Provisional Patent Application Ser. No. 60/947,019 filed Jun. 29, 2007, which is incorporated herein by reference in its entirety.

FIELD OF THE INVENTION

The present invention generally relates to a catalytic procedure for the stereoselective catalytic ring opening of aziridines.

BACKGROUND OF THE INVENTION

Aziridines are three-membered ring nitrogen-heterocycles that are attractive substrates in the synthesis of pharmaceuticals and other products. For example, it has been proposed that aziridines be used in the preparation of oseltamivir (Tamiflu®).

Aziridines are attractive substrates in synthetic methodologies, in part, because of their potential as chiral synthons. In one such method, the aziridine is derived from a chiral precursor. In another, achiral meso-arizidines are ring-opened by chiral catalyst activation or are kinetically resolved via catalytic ring-opening. For example, Jacobsen et al., *Org. Lett.* 1999, 1, 1611-1613 reported the use of chiral chromium based catalysts in the ring-opening of aziridines with TMS-$N_3$. Shibaski et al. later reported the use of catalysts derived from lanthanides provide good enantioselectivity for this desymmetrization strategy with both TMS-CN and TMS-$N_3$ as nucleophiles. Using this approach, Shibaski et al., *J. Am. Chem. Soc.* 2006, 128, 6312-6313 synthesized oseltamivir. While such approaches provide certain advantages, they also employ metal-based catalysts with the attendant disadvantages.

SUMMARY OF THE INVENTION

Among the various aspects of the present invention is the provision of a catalytic method for the stereoselective ring-opening of important synthetic starting materials (called synthons). Such new catalytic asymmetric methods for the synthesis of 1,2-diamines are highly desired in the pharmaceutical industry. For example, these ring-opened products are highly desired chiral diamines that are important starting materials in the synthesis of drugs like Tamiflu®. Also among the various embodiments is the stereoselective catalytic process for aziridine ring opening reactions; the provision of such a process which does not employ metal-based catalysts, the provision of a process which may be used with a wide range of nucleophiles, and the provision of such a process which is, nonetheless, highly selective.

Briefly, therefore, the present invention is directed to a process for the preparation of a nucleophilic addition product of an aziridine and a nucleophile, the process comprising treating the arizidine with the nucleophile in the presence of a biaryl phosphoric acid catalyst.

Other objects and features will be in part apparent and in part pointed out hereinafter.

ABBREVIATIONS AND DEFINITIONS

The following definitions and methods are provided to better define the present invention and to guide those of ordinary skill in the art in the practice of the present invention. Unless otherwise noted, terms are to be understood according to conventional usage by those of ordinary skill in the relevant art.

The term "acyl," as used herein alone or as part of another group, denotes the moiety formed by removal of the hydroxy group from the group —COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (—O—), e.g., RC(O)O— wherein R is as defined in connection with the term "acyl."

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl, and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halide," "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters, ethers, and thioethers.

DETAILED DESCRIPTION OF THE INVENTION

One aspect of the present invention is directed to a stereoselective catalytic process for aziridine ring opening reactions. Advantageously, the process does not employ metal-based catalysts. It may also be used with a wide range of nucleophiles. In general, the process comprises treating an arizidine with a nucleophile in the presence of a biaryl phosphoric acid catalyst to produce a nucleophilic addition product.

In one embodiment, the aziridines are meso- in nature and the chiral phosphoric acid catalyzes the addition of the nucleophile to provide the asymmetric ring opened product. In an alternative embodiment, the starting aziridines are racemic in nature, the chiral phosphoric acid catalyzes a kinetic resolution of the original racemic aziridine and also provide a chiral ring opened product simultaneously.

In one preferred embodiment, the aziridine corresponds to Formula A and the nucleophilic addition product corresponds to Formula B

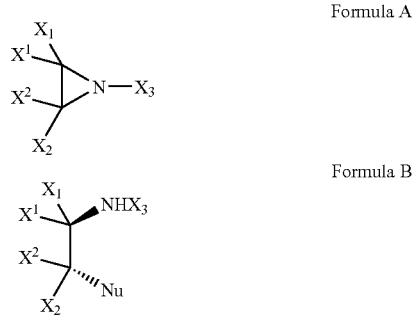

Formula A

Formula B wherein
Nu is a nucleophile residue
$X_1$, $X^1$, $X_2$ and $X^2$ are independently hydrogen, hydrocarbyl, substituted hydrocarbyl, or heterocyclo, and, optionally, (i) $X_1$ and $X_2$ and the ring carbon atoms to which they are respectively bonded, in combination, form a fused ring system, (ii) $X_1$ and $X^1$ and the ring carbon atom to which they are bonded, in combination, form a spiro ring, or (ii) $X_2$ and $X^2$ and the ring carbon atom to which they are bonded, in combination, form a spiro ring, and $X_3$ is hydrocarbyl, substituted hydrocarbyl, heterocyclo, silyl, acyl, or amine protecting group.

In one preferred embodiment, $X^1$ and $X^2$ are hydrogen and the aziridine corresponds to Formula I and the nucleophilic addition product corresponds to Formula II

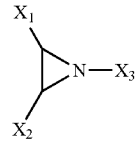

Formula I

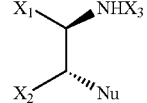

Formula II wherein
Nu is a nucleophile residue
$X_1$ and $X_2$ are independently hydrogen, hydrocarbyl, substituted hydrocarbyl, or heterocyclo, or $X_1$ and $X_2$ and the ring carbon atoms to which they are respectively bonded, in combination, form a fused ring system.

$X_3$ is hydrocarbyl, substituted hydrocarbyl, heterocyclo, silyl, acyl, or amine protecting group.

In one embodiment, the aziridine corresponds to Formula I and $X_1$ and $X_2$ are independently hydrocarbyl or substituted. Thus, for example, $X_1$ or $X_2$, or both $X_1$ and $X_2$ may be lower alkyl such as methyl, ethyl, propyl, butyl, pentyl, or hexyl. By way of further example, $X_1$ or $X_2$, or both $X_1$ and $X_2$ may be substituted lower alkyl such as substituted methyl, ethyl, propyl, butyl, pentyl, or hexyl wherein the alkyl group is substituted with a heteroatom such as nitrogen, oxygen, silicon, phosphorous, boron, sulfur, or a halogen. These substituents include halogen, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters, ethers, and thioether. By way of further example, $X_1$ or $X_2$, or both $X_1$ and $X_2$ may be alkenyl, alkynyl or aryl. By way of further example, $X_1$ or $X_2$, or both $X_1$ and $X_2$ may be substituted alkenyl, substituted alkynyl or substituted aryl wherein the alkenyl, alkynyl, or aryl moiety is substituted with a heteroatom such as nitrogen, oxygen, silicon, phosphorous, boron, sulfur, or a halogen.

In another embodiment, the aziridine corresponds to Formula I and $X_1$ and $X_2$ and the ring carbon atoms to which they are respectively bonded, in combination, form a fused ring system as depicted in Formulae IA and IIA:

Formula IA

Formula IIA

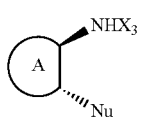

wherein $X_3$ is as previously defined and A is a fused carbocyclic or heterocyclic ring system. This ring system may be monocyclic or polycyclic (see, e.g., Formulae IB and IIB). In one embodiment, for example, A is monocyclic, contains 4 to 7 ring atoms, and is carbocyclic or heterocyclic. When A is a monocyclic heterocycle, it may contain 4 to 7 ring atoms selected from the group consisting of carbon, oxygen, nitrogen, and sulfur. In addition, A may be fully saturated, partially unsaturated or aromatic. For example, A may be a monocyclic, fused cyclobutyl, cyclopentyl, cyclohexyl, or cycloheptyl ring, optionally substituted with a heteroatom as described elsewhere herein. By way of further example, A may be a fused, optionally substituted 5-membered heterocyclic ring or an optionally substituted 6-membered heterocylic ring. Exemplary 5-membered and 6-membered heterocycles include pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, homopiperidinyl, 1,2,3,6-tetrahydropyridinyl, 2-pyrrolinyl, 3-pyrrolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl. Exemplary 5-membered and 6-membered aromatic heterocyclic groups include imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridyl, pyridazinyl, triazinyl, oxadiazolyl, thiadiazolyl, and furazanyl. By way of further example, A may be an optionally substituted, fused cyclohexyl or phenyl ring with the substituent(s) being selected from lower alkyl, hydroxyl, alkoxyl, amino, halo, nitro and heterocyclo. In another embodiment, A may be an optionally substituted, fused pyridyl, pyrimidinyl, pyradizinyl, pyrizinyl, furyl, thienyl, isoxazolyl, or pyrrolyl; thus, for example, A may be an optionally substituted, fused pyridyl, furyl, thienyl, or pyrrolyl ring with the substituent(s) being selected from lower alkyl, hydroxyl, alkoxyl, amino, halo, and nitro. Exemplary aziridines corresponding to Formula IA include:

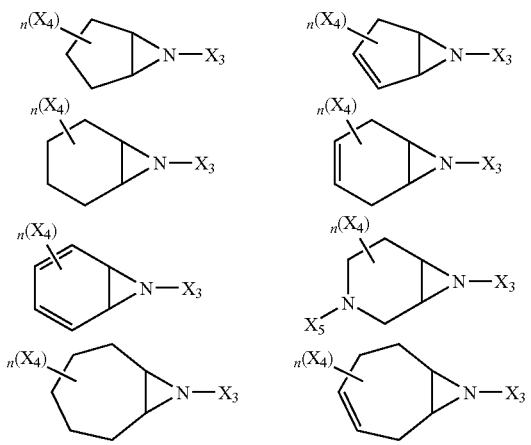

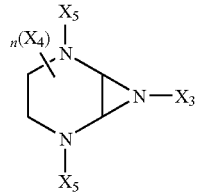
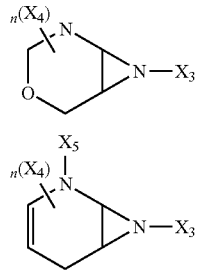
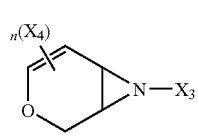
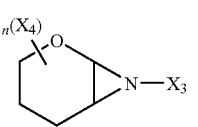
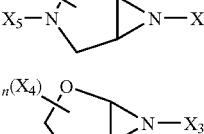
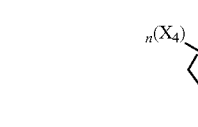
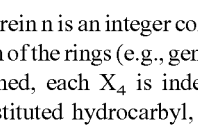

wherein n is an integer consistent with the rules of valence for each of the rings (e.g., generally from 1-5), $X_3$ is as previously defined, each $X_4$ is independently hydrogen, hydrocarbyl, substituted hydrocarbyl, halogen, heterocyclo, hydrocarbyloxy, hydroxy, keto, acyl, acyloxy, nitro, amino, amido, or thiol, and each $X_5$ is independently hydrogen, hydrocarbyl, substituted hydrocarbyl, heterocyclo, or acyl. In one embodiment, $X_5$ is hydrogen or acyl. Certain of these exemplified structures are meso- in nature and others are racemic and as described elsewhere herein, the chiral phosphoric acid catalyzes the addition of the nucleophile to provide an asymmetric (for meso-type structures) or chiral (for racemic type structures) nucleophilic addition product.

In another embodiment, A is a fused polycyclic ring system. Stated differently, in this embodiment the aziridine corresponds to Formula I, the nucleophilic addition product corresponds to Formula II, and $X_1$ and $X_2$ and the ring carbon atoms to which they are respectively bonded, in combination, form a polycyclic fused ring system. This is depicted, for example, Formulae IB and IIB:

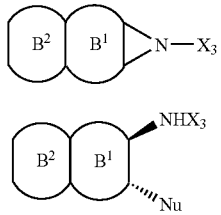

Formula IB

Formula IIB wherein $X_3$ is as previously defined, and $B^1$ and $B^2$ are each monocyclic, independently containing 4 to 7 ring atoms, and independently being carbocyclic or heterocyclic. When $B^1$ or $B^2$ is a heterocycle, it may contain 4 to 7 ring atoms selected from the group consisting of carbon, oxygen, nitrogen, and sulfur. In addition, $B^1$ and $B^2$ may, independently be fully saturated, partially unsaturated or aromatic. For example, $B^1$ and $B^2$ may, independently, be a monocyclic, fused cyclobutyl, cyclopentyl, cyclohexyl, or cycloheptyl ring, optionally substituted with a heteroatom as described elsewhere herein. By way of further example, $B^1$ or $B^2$ may be a fused, optionally substituted 5-membered heterocyclic ring or an optionally substituted 6-membered heterocylic ring. Exemplary 5-membered and 6-membered heterocycles include pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, homopiperidinyl, 1,2,3,6-tetrahydropyridinyl, 2-pyrrolinyl, 3-pyrrolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl. Exemplary 5-membered and 6-membered aromatic heterocyclic groups include imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridyl, pyridazinyl, triazinyl, oxadiazolyl, thiadiazolyl, and furazanyl. By way of further example, $B^1$ and $B^2$ may be an optionally substituted, fused cyclohexyl or phenyl ring with the substituent(s) being selected from lower alkyl, hydroxyl, alkoxyl, amino, halo, nitro and heterocyclo. In another embodiment, $B^1$ and $B^2$ may independently be an optionally substituted, fused pyridyl, pyrimidinyl, pyradizinyl, pyrizinyl, furyl, thienyl, isoxazolyl, or pyrrolyl; thus, for example, $B^1$ and $B^2$ may independently be an optionally substituted, fused pyridyl, furyl, thienyl, or pyrrolyl ring with the substituent(s) being selected from lower alkyl, hydroxyl, alkoxyl, amino, halo, and nitro. Exemplary aziridines corresponding to Formula IB include:

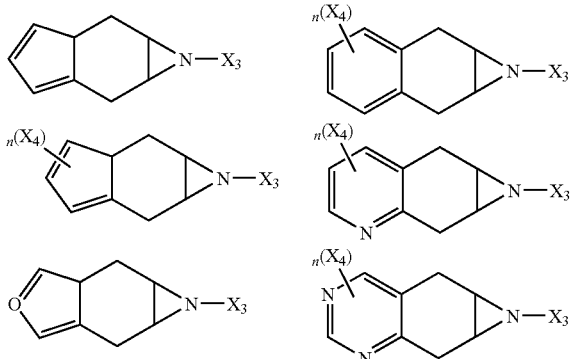

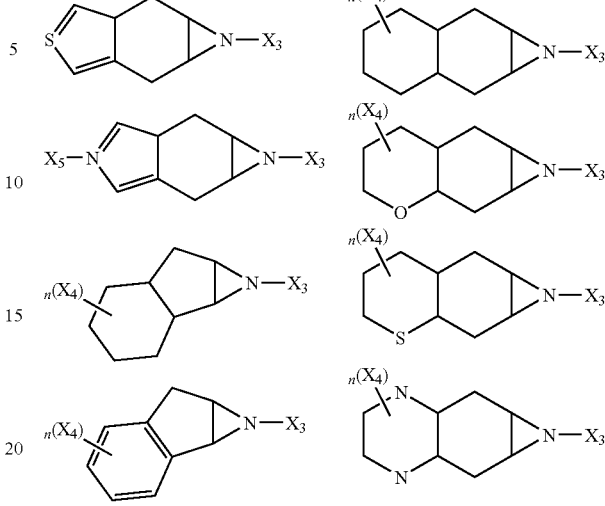

wherein n is an integer consistent with the rules of valence for each of the rings (e.g., generally from 1-5), $X_3$ is as previously defined, each $X_4$ is independently hydrogen, hydrocarbyl, substituted hydrocarbyl, halogen, heterocyclo, hydrocarbyloxy, hydroxy, keto, acyl, acyloxy, nitro, amino, amido, or thiol, and each $X_5$ is independently hydrogen, hydrocarbyl, substituted hydrocarbyl, heterocyclo, or acyl. In one embodiment, $X_5$ is hydrogen or acyl. Certain of these exemplified structures are meso- in nature and others are racemic and as described elsewhere herein, the chiral phosphoric acid catalyzes the addition of the nucleophile to provide an asymmetric (for meso-type structures) or chiral (for racemic type structures) nucleophilic addition product.

In general, $X_3$ may be any substituent that does not interfere with the chemical stability of the aziridine. In one embodiment, $X_3$ is hydrocarbyl; for example, $X_3$ may be alkyl, alkenyl, alkynyl, aryl, vinyl, allyl, or the like. In another embodiment, $X_3$ is substituted hydrocarbyl wherein the hydrocarbyl group is substituted with a heteroatom such as nitrogen, oxygen, silicon, phosphorous, boron, sulfur, or a halogen; exemplary substituents include halogen, heterocyclo, alkoxy, alkenoxy, alkynoxy, aryloxy, hydroxy, keto, acyl, acyloxy, nitro, amino, amido, nitro, cyano, thiol, ketals, acetals, esters, ethers, and thioether. In another embodiment, $X_3$ is silyl, such as trialkylsilyl, dialkylarylsilyl, or triarylsilyl. In another embodiment, $X_3$ is any substitutent conventionally used to hinder the reactivity of an amino group as described in Green, T., "Protective Groups in Organic Synthesis," Chapter 7, John Wiley and Sons, Inc., 1991, 315-385.

In one preferred embodiment, $X_3$ is acyl. For example, in this embodiment, $X_3$ may have the formula —C(O)A wherein A is hydrocarbyl, substituted hydrocarbyl, or heterocyclo. By way of further example, A may be optionally substituted alkyl, alkenyl, alkyl, or aryl. By way of further example, A may be phenyl or substituted phenyl. By way of further example, A may be substituted phenyl, with the phenyl substituents being selected from alkyl, substituted alkyl, aryl, substituted aryl, halo, nitro, amino, acyl, hydroxy, and alkoxy. By way of further example, A may be nitro, fluoro, or trifluoromethyl substituted phenyl. By way of further example, A may be heterocyclo.

In general, the nucleophile residue, Nu, is preferably a nucleophile residue selected from the group consisting of carbon, oxygen, nitrogen, sulfur, or silyl based nucleophile residues. Carbon nucleophiles include alkyl and aryl carbanions, enamines, enolates, olefins and cyanide. Oxygen nucleophiles include alkyl and aryl alcohols, hydroxyl, and carboxylates. Sulfur nucleophiles include alkyl and arylsulfides, and thioacyl acids. Nitrogen nucleophiles include amines, amides and azides. Halogen nucleophiles include chloride, bromide, fluoride and iodide. Hydrogen nucleophiles include hydrogen from hydrogenation sources and hydrides. Other miscellaneous nucleophiles include cycloaddition nucleophiles, and heteroatom nucleophiles such as phosphorous nucleophiles, silanes, selenols, and cobalt nucleophiles. Organometallic reagents such as organocuprates, organozincs, organolithiums, Grignard reagents, enolates, acetylides, and the like may, under appropriate reaction conditions, be suitable nucleophiles. Hydride may also be a suitable nucleophile when reduction of the substrate is desired In one preferred embodiment, the stereoselective ring opening of the aziridine proceeds as depicted in Reaction Scheme 1

Reaction Scheme 1

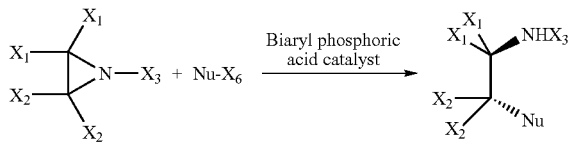

wherein Nu, $X_1$, $X^1$, $X_2$, $X^2$ and $X_3$ are as defined in connection with Formula I and IA and $X_6$ is a leaving group for the nucleophile. Exemplary nucleophile leaving groups ($X_6$) include silyl groups when the nucleophile is azide, cyanide or halide or a proton when the nucleophile is an alcohol. In one embodiment, the leaving group is a silyl leaving group such as trialkylsilyl (e.g., trimethylsilyl, triethylsilyl, etc.) or dialkylarylsilyl (e.g., dimethylphenylsilyl).

In one embodiment, $X_1$, $X^1$, $X_2$, and $X^2$ are selected such that the aziridine is meso- in nature. In this embodiment, the chiral phosphoric acid catalyzes the addition of the nucleophile to provide an asymmetric nucleophilic addition product. In an alternative embodiment, $X_1$, $X^1$, $X_2$, and $X^2$ are selected such that the aziridine is racemic in nature, the chiral phosphoric acid catalyzes a kinetic resolution of the original racemic aziridine and also provides a chiral nucleophilic addition product.

When $X_1$ and $X_2$ are hydrogen, the stereoselective ring opening of the aziridine proceeds as depicted in Reaction Scheme 2

Reaction Scheme 2

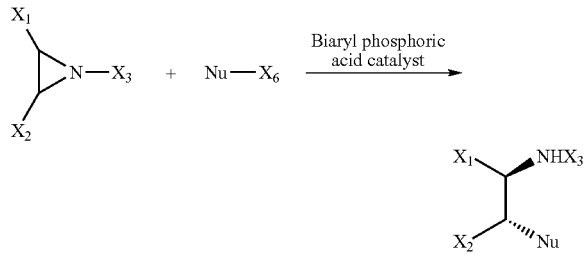

wherein Nu, $X_1$, $X^1$, $X_2$, $X^2$ and $X_3$ are as defined in connection with Formula I and IA and $X_6$ is a leaving group for the nucleophile. Exemplary nucleophile leaving groups ($X_6$) include silyl groups when the nucleophile is azide, cyanide or halide or a proton when the nucleophile is an alcohol. In one embodiment, the leaving group is a silyl leaving group such as trialkylsilyl (e.g., trimethylsilyl, triethylsilyl, etc.) or dialkylarylsilyl (e.g., dimethylphenylsilyl). In one embodiment, $X_1$ and $X_2$ are selected such that the aziridine is meso- in nature. In this embodiment, the chiral phosphoric acid catalyzes the addition of the nucleophile to provide the asymmetric ring opened product. In an alternative embodiment, $X_1$ and $X_2$ are selected such that the aziridine is racemic in nature, the chiral phosphoric acid catalyzes a kinetic resolution of the original racemic aziridine and also provide a chiral ring opened product simultaneously.

In one embodiment, the nucleophile is an amine. In this embodiment, for example, the nucleophile may be $NHD_1D_2$ wherein $D_1$ and $D_2$ are independently hydrogen, hydrocarbyl, substituted hydrocarbyl or heterocyclo. Thus, for example, the nucleophile may be ammonia. By way of further example, the nucleophile may be a primary amine ($NH_2D_1$ wherein $D_1$ is optionally substituted alkyl, alkenyl, alkynyl, aryl or heterocyclo) or a secondary amine ($NHD_1D_2$ wherein $D_1$ and $D_2$ are independently optionally substituted alkyl, alkenyl, alkynyl, aryl or heterocyclo). In one embodiment, $D_1$ and $D_2$ are independently hydrogen, alkyl, aryl or heterocyclo; thus, for example, one of $D_1$ and $D_2$ may be heterocyclo and the other is hydrogen, alkyl or aryl. By way of further example, $D_1$ and $D_2$ are independently hydrogen, alkyl or aryl.

In another embodiment, the nucleophile is an amide. In this embodiment, for example, the nucleophile may be $D_1C(O)NHD_2$ wherein $D_1$ and $D_3$ are independently hydrogen, hydrocarbyl, substituted hydrocarbyl or heterocyclo. In one embodiment, $D_1$ and $D_2$ are independently hydrogen, alkyl, aryl or heterocyclo; thus, for example, one of $D_1$ and $D_2$ may be heterocyclo and the other is hydrogen, alkyl or aryl. By way of further example, $D_1$ and $D_2$ are independently alkyl or aryl.

In one embodiment, the nucleophile is a silylazide and the nucleophile residue is azide ($-N_3$). Exemplary silyl azides include trialkylsilylazides, triarylsilylazides, and alkylarylsilylazides.

In another embodiment, the nucleophile is an alcohol and the residue is an alkoxy group, $-OT_1$, wherein $T_1$ is hydrocarbyl, substituted hydrocarbyl, or heterocyclo. Thus, for example, $T_1$ may be optionally substituted alkyl, alkenyl, alkynyl, aryl, or combinations thereof (e.g., alkaryl such as benzyl). In one embodiment, $T_1$ is alkyl. In another, $T_1$ is alkenyl. In yet another, $T_1$ is alkynyl. In yet another, $T_1$ is aryl. In yet another, $T_1$ is heterocyclo. In yet another, $T_1$ is heteroaromatic.

In another embodiment, the nucleophile is a mercaptan having the formula $HSD_1$ wherein $D_1$ is hydrocarbyl, substituted hydrocarbyl, or heterocyclo. For example, in one embodiment, $D_1$ is optionally substituted alkyl, alkenyl, alkynyl, aryl or heterocyclo). By way of further example, $D_1$ may be alkyl, alkenyl, alkynyl, aryl or heterocyclo).

In another embodiment, the nucleophile is a silylcyanide and the nucleophile residue is cyano ($-CN$). Exemplary silylcyanides include trialkylsilylcyanides, triarylsilylcyanides, and alkylarylsilylcyanides.

In another embodiment, the nucleophile is a halosilyl and the nucleophile residue is halo (chloro, bromo, fluoro, or iodo). Exemplary halosilyls include halotrialkylsilyls, halotriarylsilyls, and haloalkylarylsilyls.

In one embodiment of the present invention, chiral phosphoric acids catalyze the ring-opening of meso-aziridines with excellent enantioselectivity and in high yield using TMS-$N_3$ as the nucleophile. Such a reaction provides a procedure whereby synthetically important, chiral 1,2-diamine analogues can be readily formed.

In general, the biaryl phosphoric acid catalyst corresponds to Formula III

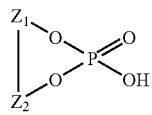

Formula III wherein $Z_1$ and $Z_2$ are independently aryl. Thus, for example, $Z_1$ and $Z_2$ may be optionally substituted phenyl, naphthyl or other fused aromatic rings. In one embodiment, the catalyst generally corresponds to biaryl phosphoric acid 1; in this embodiment, biaryl phosphoric acid 1 is preferably a biaryl phosphoric acid corresponding to biaryl phosphoric acid 1A or 1B:

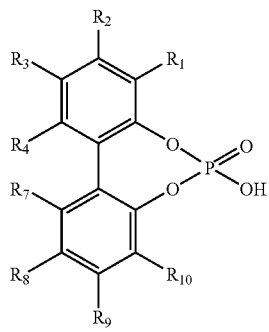

Biaryl Phosphoric Acid 1

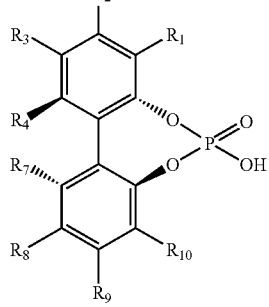

Biaryl Phosphoric Acid 1A

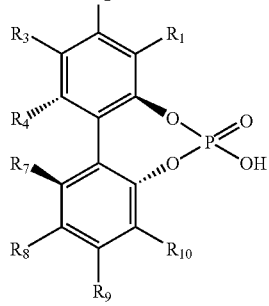

Biaryl Phosphoric Acid 1B wherein (i) $R_1$, $R_2$, $R_3$, $R_4$, $R_7$, $R_8$, $R_9$ and $R_{10}$ are independently hydrogen, hydrocarbyl, substituted hydrocarbyl, halogen, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, or thiourea, and (ii) one or more pairs of substituents, with an ortho relationship therebetween, selected from the group consisting of $R_1$, $R_2$, $R_3$, $R_4$, $R_7$, $R_8$, $R_9$ and $R_{10}$ taken together optionally represent an optionally substituted carbocyclic or heterocyclic fused ring system.

In one embodiment, the biaryl phosphoric acid catalyst comprises a fused ring system and corresponds to biaryl phosphoric acid 2; in this embodiment, biaryl phosphoric acid 2 is preferably a biaryl phosphoric acid corresponding to biaryl phosphoric acid 2A or 2B:

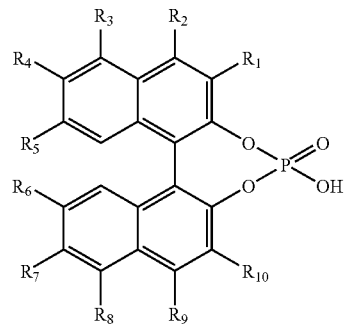

Biaryl Phosphoric Acid 2

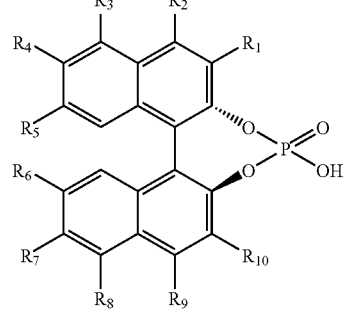

Biaryl Phosphoric Acid 2A

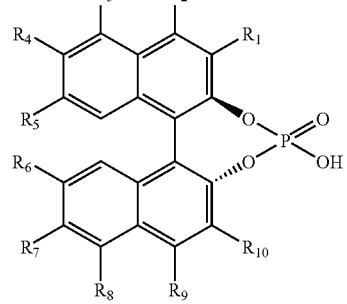

Biaryl Phosphoric Acid 2B wherein (i) $R_1$, $R_2$, $R_3$, $R_4$, $R_7$, $R_8$, $R_9$ and $R_{10}$ are as previously defined in connection with biaryl phosphoric acid I, and $R_5$ and $R_6$ are independently hydrogen, hydrocarbyl, substituted hydrocarbyl, halogen, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, or thiourea, and (ii) one or more pairs of substituents, with an ortho relationship therebetween, selected from the group consisting of $R_1$, $R_2$, $R_3$, $R_4$, $R_5$, $R_6$, $R_7$, $R_8$, $R_9$ and $R_{10}$ taken together optionally represent an optionally substituted carbocyclic or heterocyclic fused ring system.

In one embodiment, the biaryl phosphoric acid catalyst comprises a fused ring system and corresponds to biaryl phosphoric acid 3; in this embodiment, biaryl phosphoric acid 3 is preferably a biaryl phosphoric acid corresponding to biaryl phosphoric acid 3A or 3B:

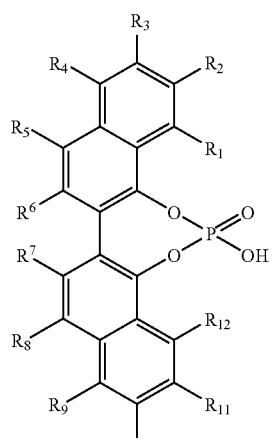

Biaryl Phosphoric Acid 3

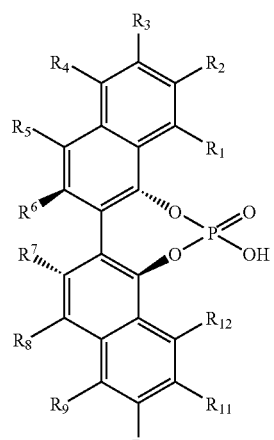

Biaryl Phosphoric Acid 3A

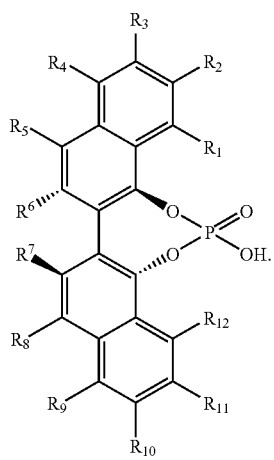

Biaryl Phosphoric Acid 3B wherein (i) $R_1$, $R_2$, $R_3$, $R_4$, $R_5$, $R_6$, $R_7$, $R_8$, $R_9$, $R_{10}$, $R_{11}$, and $R_{12}$ are independently hydrogen, hydrocarbyl, substituted hydrocarbyl, halogen, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, or thiourea, and (ii) one or more pairs of substituents, with an ortho relationship therebetween, selected from the group consisting of $R_1$, $R_2$, $R_3$, $R_4$, $R_5$, $R_6$, $R_7$, $R_8$, $R_9$, $R_{10}$, $R_{11}$ and $R_{12}$ taken together optionally represent an optionally substituted carbocyclic or heterocyclic fused ring system.

In one embodiment, the biaryl phosphoric acid catalyst comprises a fused ring system and corresponds to biaryl phosphoric acid 4; in this embodiment, biaryl phosphoric acid 4 is preferably a biaryl phosphoric acid corresponding to biaryl phosphoric acid 4A or 4B:

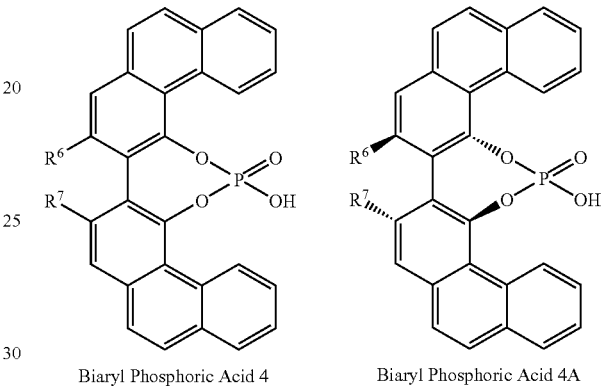

Biaryl Phosphoric Acid 4      Biaryl Phosphoric Acid 4A

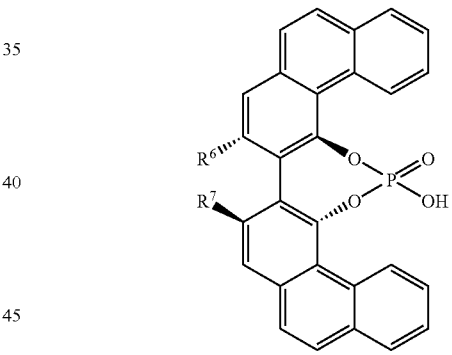

Biaryl Phosphoric Acid 4B wherein $R_6$ and $R_7$ are independently hydrocarbyl, substituted hydrocarbyl, halogen, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, or thiourea. In a preferred embodiment, $R_6$ and $R_7$ are preferably hydrocarbyl, more preferably alkyl or phenyl.

In one embodiment, the biaryl phosphoric acid catalyst comprises a fused ring system and corresponds to biaryl phosphoric acid 5; in this embodiment, biaryl phosphoric acid 5 is preferably a biaryl phosphoric acid corresponding to biaryl phosphoric acid 5A or 5B:

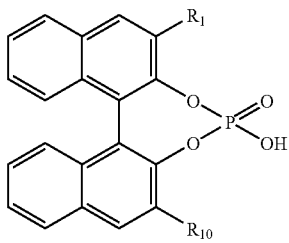

Biaryl Phosphoric Acid 5

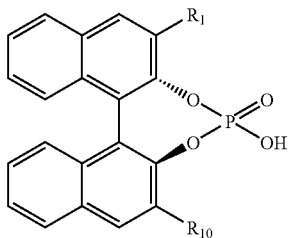

Biaryl Phosphoric Acid 5A

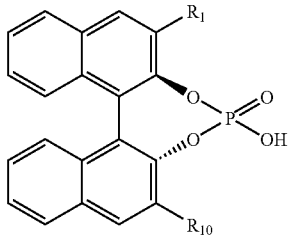

Biaryl Phosphoric Acid 5B wherein $R_1$ and $R_{10}$ are independently hydrocarbyl, substituted hydrocarbyl, halogen, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, or thiourea. In a preferred embodiment, $R_1$ and $R_{10}$ are preferably hydrocarbyl, more preferably alkyl or phenyl.

In one preferred embodiment, the biaryl phosphoric acid catalyst is VAPOL phosphoric acid (VAPOL PA-1) or VANOL phosphoric acid (VANOL PA-2):

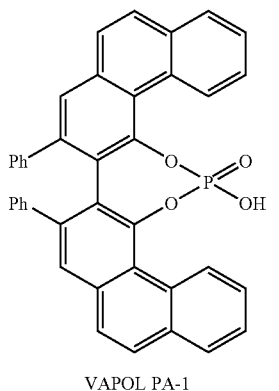
VAPOL PA-1

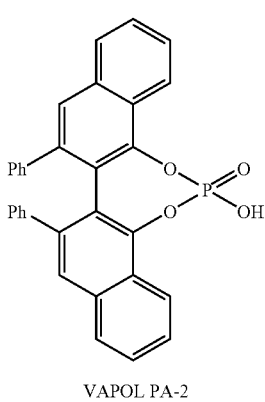
VAPOL PA-2 wherein Ph is phenyl.

Having described the invention in detail, it will be apparent that modifications and variations are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

General Procedure for the Preparation of Racemic Products Using TMS-$N_3$

The aziridine (0.25 mmol), phenylphosphinic acid, $Tf_2NH$, or a mixture of (R) and (S) VAPOL-phosphoric acid (10 to 100 mol %), were weighed into a test tube. The air was removed under vacuum and replaced with argon. TMS-$N_3$ (0.67-4 equiv.) was added via syringe to the test-tube followed by $(CH_2Cl)_2$ or $CH_2Cl_2$ (0.5 mL). The reaction was stirred at room temperature to 60° C. until product formation was significant which was monitored by TLC. The reaction was diluted with $CH_2Cl_2$, concentrated on silica gel, and purified by flash column chromatography.

General Procedure for the Enantioselective Ring Opening TMS-$N_3$

To a flame-dried test tube was added aziridine (0.25-0.38 mmol) and acid catalyst (10 mol %). The air was removed and replaced with argon. TMS-$N_3$ (0.25-1 mmol) was added via syringe to the test-tube followed by 1,2-dichloroethane (0.25-1.0 mL). The reaction was stirred at room temperature to 60° C. and monitored by TLC. The reaction was diluted with $CH_2Cl_2$, concentrated on silica gel, and purified by flash column chromatography.

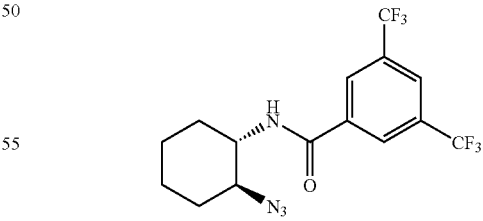

1-Azido-2-[N-(3,5-Bis-trifluoromethylbenzoyl)amino]-cyclohexane To a flame-dried test tube was added 7-(3,5-Bis-trifluoromethylbenzoyl)-7-azabicyclo[3.1.0]heptane (0.128 g, 3.38 mmol) and (S)-VAPOL phosphoric acid (15 mg, 10 mol %). The air was removed and replaced with argon. TMS-$N_3$ (33 μL, 0.25 mmol) was added via syringe to the test-tube followed by 1,2-dichloroethane (0.5 mL). The reaction was stirred at ambient temperature for 21 h. The reaction was diluted with CH₂Cl₂, concentrated on silica gel, and purified by flash column chromatography with hexanes/EtOAc. Recovered white solid (0.093 g, 97%). Mp=138.9-139.4° C. HPLC analysis: Chiralcel AS-H (hexane/iPrOH=90/10, 1.0 mL/min), t$_{r-minor}$ 6.15 min, t$_{r-major}$ 8.65 min. 1H NMR (500 MHz, CDCl₃): δ1.28-1.41 (m, 3H), 1.47-1.55 (m, 1H), 1.76 (m, 1H), 1.87 (m, 1H), 2.16 (m, 2H), 3.27 (m, 1H), 3.95 (m, 1H), 6.34 (d, J=7.7 Hz, 1H), 7.98 (s, 1H), 8.19 (s, 2H). ¹³C NMR (125 MHz, CDCl₃):

δ 24.1, 24.2, 30.6, 31.9, 53.7, 63.5, 119.7, 121.8, 123.9, 125.0, 125.4, 127.3, 132.1 (q, J=34 Hz), 136.6, 164.6. HRMS (ESI) Calcd for C₁₅H₁₄F₆N₄O ([M+H]⁺) 381.1145, Found 381.1140. [a]²⁹$_D$+63.8 (c=1.04, CHCl₃).

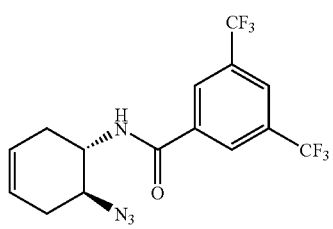

4-Azido-5-[N-(3,5-trifluoromethylbenzoyl)amino]-cyclohexene To a flame-dried test tube was added 7-(3,5-Bis-trifluoromethylbenzoyl)-7-azabicyclo[4.1.0]hept-3-ene (0.127 g, 0.38 mmol) and (S)-VAPOL phosphoric acid (15 mg, 10 mol %). The air was removed and replaced with argon. TMS-N₃ (33 µL, 0.25 mmol) was added via syringe to the test-tube followed by 1,2-dichloroethane (0.5 mL). The reaction was stirred at ambient temperature for 21 h. The reaction was diluted with CH₂Cl₂, concentrated on silica gel, and purified by flash column chromatography with hexanes/EtOAc. Recovered white solid (0.080 g, 84%). Mp=126.3-128.4° C. HPLC analysis: Chiralcel AS-H (hexane/iPrOH=95/5, 1.0 mL/min), t$_{r-minor}$ 11.33 min t$_{r-major}$ 18.73 min. 1H NMR (500 MHz, CDCl₃): δ2.16-2.25 (m, 2H), 2.49-2.59 (m, 2H), 3.72 (m, 1H), 4.20 (m, 1H), 5.62 (m, 2H), 7.24 (d, J=8.0 Hz, 1H), 7.90 (s, 1H), 8.16 (s, 2H). ¹³C NMR (125 MHz, CDCl₃ δ 29.9, 30.8, 49.8, 59.2, 119.5, 121.7, 123.8, 124.6, 124.9, 126.0, 127.4, 127.4, 13 2.0 (q, J=34 Hz), 136.3, 165.2. HRMS (ESI) Calcd for C₁₅H₁₂F₆N₄O ([M+H]⁺) 379.0988, Found 379.0997. [a]²⁹$_D$+70.3 (c=1.10, CHCl₃).

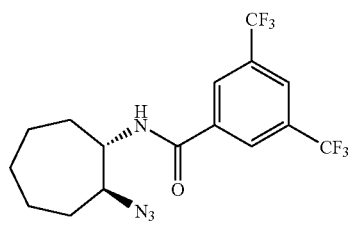

trans-1-Azido-2-[N-(3,5-Bis-trifluoromethylbenzoyl) amino]-cycloheptane To a flame-dried test tube was added 8-(3,5-Bis-trifluoromethylbenzoyl)-8-azbicyclo[5.1.0]octane (0.088 g, 0.25 mmol) and (S)-VAPOL phosphoric acid (15 mg, 10 mol %). The air was removed and replaced with argon. TMS-N₃ (66 µL, 0.50 mmol) was added via syringe to the test-tube followed by 1,2-dichloroethane (0.5 mL). The reaction was stirred at ambient temperature for 91 h. The reaction was diluted with CH₂Cl₂, concentrated on silica gel, and purified by flash column chromatography with hexanes/EtOAc. Recovered white solid (0.063 g, 64%). Mp=139.3-140.9° C. HPLC analysis: Chiralcel AS-H (hexane/iPrOH=90/10, 1.0 mL/min), t$_{r-minor}$ 5.35 min, t$_{r-major}$ 8.27 min. 1H NMR (500 MHz, CDCl₃): δ 1.51-1.57 (m, 3H), 1.60-1.81 (m, 5H), 1.89-1.99 (m, 2H), 3.53 (m, 1H), 4.02 (m, 1H), 7.17 (d, J=7.8, 1H), 7.91 (s, 1H), 8.17 (s, 2H). ¹³C NMR (125 MHz, CDCl₃): δ 22.9, 23.8, 27.3, 30.5, 31.8, 56.5, 66.5, 119.5, 121.7, 128.9, 124.8, 126.0, 127. 4, 131.9 (q, J=34 Hz), 136.5, 164.6. HRMS (ESI) Calcd for C₁₆H₁₆F₆N₄O ([M+H]⁺) 395.1301, Found 395.1302. [a]²⁹$_D$+36.9 (c=1.04, CHCl₃).

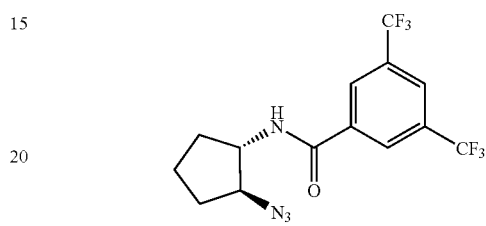

trans-1-Azido-2-[N-(3,5-Bis-trifluoromethyl benzoyl) amino]-cyclopentane To a flame-dried test tube was added 6-(3,5-Bis-trifluoromethylbenzoyl)-6-azabicyclo[3.1.0]hexane (0.12 g, 0.38 mmol) and (S)-VAPOL phosphoric acid (15 mg, 10 mol %). The air was removed and replaced with argon. TMS-N₃ (33 µL, 0.25 mmol) was added via syringe to the test-tube followed by 1,2-dichloroethane (0.5 mL). The reaction was stirred at ambient temperature for 48 h. The reaction was diluted with CH₂Cl₂, concentrated on silica gel, and purified by flash column chromatography with hexanes/EtOAc. Recovered colorless oil (0.063 g, 84%). Mp=99.5-100.5° C. HPLC analysis: Chiralcel AS-H (hexane/iPrOH=95/5, 1.0 mL/min), t$_{r-minor}$ 12.16 min, t$_{r-major}$ 14.04 min. 1H NMR (500 MHz, CDCl₃): δ1.62-1.82 (m, 4H), 2.02-2.08 (m, 1H), 2.14-2.22 (m, 1H), 3.90 (q, J=6.7 Hz, 1H), 4.25 (m, 1H), 7.41 (d, J=7.7 Hz, 1H), 7.86 (s, 1H), 8.12 (s, 2H). ¹³C NMR (125 MHz, CDCl₃):

δ 16.9, 18.7, 49.5, 61.7, 119.6, 121.8, 123.9, 125.1, 127.2, 132.2 (q, J=34 Hz), 136.4, 164.3. HRMS (ESI) Calcd for C₁₄H₁₂F₆N₄O ([M+H]⁺) 367.0988, Found 367.0988. [a]²⁹$_D$+ 40.2 (c=1.01, CHCl₃).

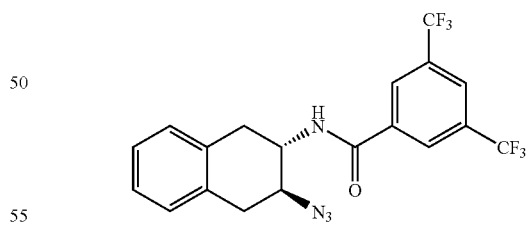

trans-2-Azido-3-[N-(3,5-Bis-trifluoromethylbenzoyl) amino]-tetralin To a flame-dried test tube was added N-(3,5-Bis-trifluoromethylbenzoyl)-2,3-iminotetralin (0.096 g, 0.25 mmol) and (S)-VAPOL phosphoric acid (15 mg, 10 mol %). The air was removed and replaced with argon. TMS-N₃ (66 µL, 0.50 mmol) was added via syringe to the test-tube followed by 1,2-dichloroethane (1.0 mL). The reaction was stirred at ambient temperature for 48 h. The reaction was diluted with CH₂Cl₂, concentrated on silica gel, and purified by flash column chromatography with hexanes/CH₂Cl₂. Recovered white solid (0.096 g, 90%). Mp=146.8-147.6° C.

HPLC analysis: Chiralcel AS-H (hexane/iPrOH=90/10, 1.0 mL/min), $t_{r\text{-}minor}$ 8.05 min, $t_{r\text{-}major}$ 15.71 min. 1H NMR (500 MHz, CDCl$_3$): δ 2.89 (m, 1H), 3.0 (m, 1H), 3.23 (dd, 11.4, 5.3 Hz, 1H), 3.39 (dd, 11.3, 5.4 Hz, 1H), 3.98 (m, 1H), 4.41 (m, 1H), 6.62 (d, J=7.6 Hz, 1H), 7.05-7.18 (m, 4H), 7.97 (s, 1H), 8.18 (s, 2H). 13C NMR (125 MHz, CDCl$_3$):

δ 33.1, 33.9, 50.3, 59.4, 119.5, 121.7, 123.9, 125.2, 126.0, 126.9, 127.3, 128.9, 128.9, 13 2.3 (q, J=34 Hz), 136.2, 164.9. HRMS (ESI) Calcd for C$_{19}$H$_{14}$F$_6$N$_4$O ([M+H]$^+$) 429.1145, Found 429.1146. [a]$^{29}_D$+53.3 (c=1.07, CHCl$_3$).

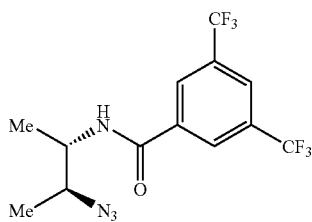

anti-2-Azido-3-[N-(3,5-Bis-trifluoromethylbenzoyl) amino]-butane To a flame-dried test tube was added cis-1-(3,5-Bis-trifluoromethylbenzoyl)-2,3-dimethylaziridine (0.118 g, 0.38 mmol) and (S)-VAPOL phosphoric acid (15 mg, 10 mol %). The air was removed and replaced with argon. TMS-N$_3$ (33 µL, 0.25 mmol) was added via syringe to the test-tube followed by 1,2-dichloroethane (0.5 mL). The reaction was stirred at ambient temperature for 21 h. The reaction was diluted with CH$_2$Cl$_2$, concentrated on silica gel, and purified by flash column chromatography with hexanes/EtOAc. Recovered colorless oil (0.077 g, 88%). Mp=50.7-51.4° C. HPLC analysis: Chiralcel OD-H (hexane/iPrOH=95/5, 1.0 mL/min), $t_{r\text{-}minor}$ 5.76 min, $t_{r\text{-}major}$ 6.96 min. 1H NMR (500 MHz, CDCl$_3$): δ 1.31 (m, 6H), 3.74 (m, 1H), 4.29 (m, 1H), 6.34 (brs, 1H), 7.98 (s, 1H), 8.17 (s, 2H). 13C NMR (125 MHz, CDCl$_3$):

δ 16.9, 18.7, 49.5, 61.7, 119.6, 121.8, 123.9, 125.1, 127.2, 132.2 (q, J=34 Hz), 136.4, 164.3. HRMS (ESI) Calcd for C$_{13}$H$_{12}$F$_6$N$_4$O ([M+H]$^+$) 355.0988, Found 355.0985. [a]$^{29}_D$+28.3 (c=1.15, CHCl$_3$).

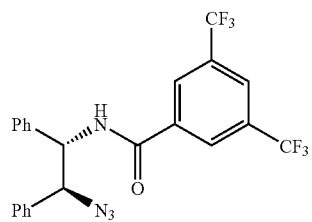

anti-1-Azido-2-[N-(3,5-Bis-trifluoromethylbenzoyl) amino]-1,2-diphenylethane To a flame-dried test tube was added cis-1-(3,5-Bis-trifluoromethylbenzoyl)-2,3-diphenylaziridine (0.16 g, 0.38 mmol) and (S)-VAPOL phosphoric acid (15 mg, 10 mol %). The air was removed and replaced with argon. TMS-N$_3$ (33 µL, 0.25 mmol) was added via syringe to the test-tube followed by 1,2-dichloroethane (1.0 mL). The reaction was stirred at ambient temperature for 48 h. The reaction was diluted with CH$_2$Cl$_2$, concentrated on silica gel, and purified by flash column chromatography with hexanes/EtOAc. Recovered white solid (0.113 g, 95%). Mp=140.3-11.0° C. HPLC analysis: Chiralcel AS-H (hexane/iPrOH=98/2, 1.0 mL/min), $t_{r\text{-}major}$ 13.49 min, $t_{r\text{-}minor}$ 20.61 min. 1H NMR (500 MHz, CDCl$_3$): δ 4.97 (d, J=6.1 Hz, 1H), 5.48 (t, J=6.6 Hz, 1H), 7.21-7.31 (m, 10H), 7.44 (brs, 1H), 7.90 (s, 1H), 8.09 (s, 2H). 13C NMR (125 MHz, CDCl$_3$):

δ 58.8, 71.6, 119.5, 121.6 123.8, 125.1, 125.9, 126.9, 127.1, 127.3, 127.3, 128.1, 128.6, 128.8, 132.0 (q, J=34 Hz), 136.2, 164.5. HRMS (ESI) Calcd for C$_{23}$H$_{16}$F$_6$N$_4$O ([M+Na]$^+$) 501.1121, Found 501.1128. [a]$^{29}_D$+33.0 (c=1.05, CHCl$_3$).

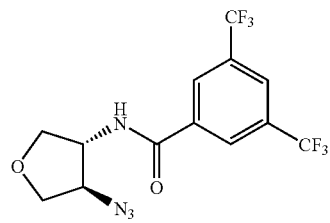

trans-3-Azido-4-[N-(3,5-Bis-trifluoromethylbenzoyl) amino]-tetrahydrofuran To a flame-dried test tube was added 3-Oxa-6-(3,5-Bis-trifluoromethylbenzoyl)-6-azbicyclo [3.1.0]hexane (0.081 g, 0.25 mmol) and (S)-VAPOL phosphoric acid (15 mg, 10 mol %). The air was removed and replaced with argon. TMS-N$_3$ (132 µL, 1.0 mmol) was added via syringe to the test-tube followed by 1,2-dichloroethane (0.25 mL). The reaction was stirred at ambient temperature for 48 h. The reaction was diluted with CH$_2$Cl$_2$, concentrated on silica gel, and purified by flash column chromatography with CH$_2$Cl$_2$/ether. Recovered white solid (0.045 g, 49%). Mp=103.3-104.6° C. HPLC analysis: Chiralcel AS-H (hexane/iPrOH=98/2, 0.75 mL/min), $t_{r\text{-}minor}$ 30.39 min, $t_{r\text{-}major}$ 32.55 min. 1H NMR (500 MHz, CDCl$_3$): δ 3.68 (dd, J=6.8 Hz, 1H), 3.89 (m, 1H), 4.03-4.07 (m, 1H), 4.11-4.18 (m, 1H), 4.19 (m, 1H), 4.56 (m, 1H) 7.01 (br s, 1H), 7.98 (s, 1H), 8.21 (s, 2H). 13C NMR (125 MHz, CDCl$_3$):

δ 57.4, 66.2, 70.9, 71.5, 119.1, 121.7, 123.8, 125.4, 126.0, 127.4, 132.2 (q, J=34 Hz), 135.4, 164.7. HRMS (ESI) Calcd for C$_{13}$H$_{10}$F$_6$N$_4$O$_2$ ([M+H]$^+$) 369.0781, Found 369.0781. [a]$^{29}_D$+42.7 (c=1.04, CHCl$_3$).

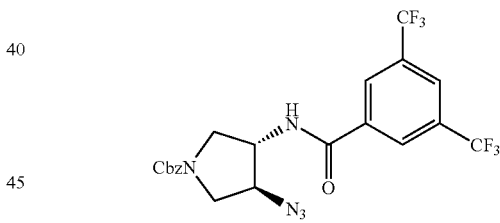

trans-1-Carbobenzyloxy-3-azido-4-[N-(3,5-Bis-trifluoromethylbenzoyl)amino]pyrrolidine To a flame-dried test tube was added 3-Carbobenzyloxy-6-(3,5-Bis-trifluoromethylbenzoyl)-3,6-diazbicyclo[3.1.0]hexane (0.110 g, 0.25 mmol) and (S)-VAPOL phosphoric acid (15 mg, 10 mol %). The air was removed and replaced with argon. TMS-N$_3$ (132 µL, 1.0 mmol) was added via syringe to the test-tube followed by 1,2-dichloroethane (0.5 mL). The reaction was stirred at ambient temperature for 96 h. The reaction was diluted with CH$_2$Cl$_2$, concentrated on silica gel, and purified by flash column chromatography with CH$_2$Cl$_2$/ether. Recovered white solid (0.122 g, 96%). Mp=47.0-48.4° C. HPLC analysis: Chiralcel OD-H (hexane/iPrOH=95/5, 1.0 mL/min), $t_{r\text{-}major}$ 10.79 min, $t_{r\text{-}minor}$ 28.65 min. 1H NMR (500 MHz, CDCl$_3$): δ 3.52-4.01 (m, 4H), 4.25-4.39 (m, 1H), 4.63-4.71 (m, 1H), 4.89-4.99 (m, 1H), 513-5.24 (m, 1H), 7.22-7.24 (m, 3H), 7.83 (d, J=5.5 Hz, 1H), 8.09 (m, 2H), 8.51 (m, 3H). 13C NMR (125 MHz, CDCl$_3$):

δ 41.6, 48.9, 49.2, 54.6, 54.9, 63.1, 64.0, 67.3, 67.8, 119.6, 121.8, 123.9, 125.3, 126.2, 127.6, 128.2, 128.4, 128.5, 132.1

(q, J=35 Hz), 135.1, 154.9, 164.6. HRMS (ESI) Calcd for $C_{21}H_{17}F_6N_5O_3$ ([M+H]$^+$) 502.1310, Found 502.1312. [α]$^{29}_D$+5.73 (c=1.03, CHCl$_3$).

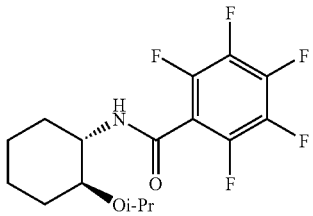

2,3,4,5,6-Pentafluoro-N-(2-isopropoxy-cyclohexyl)-benzamide To a flame-dried test tube was added (7-Aza-bicyclo[4.1.0]hept-7-yl)-pentafluorophenyl-methanone (0.044 g, 0.15 mmol) and phenylphosphinic acid (4.3 mg, 20 mol %). The air was removed and replaced with argon. Isopropanol (60 µL, 0.9 mmol) was added via syringe to the test-tube followed by dichloromethane (0.5 mL). The reaction was stirred at ambient temperature for 24 h. The reaction was diluted with CH$_2$Cl$_2$, concentrated on silica gel, and purified by flash column chromatography with hexanes/EtOAc. Recovered white solid (0.050 g, 98%). $^1$H NMR (400 MHz, CDCl$_3$): δ 1.14 (m, 6H), 1.27 (m, 4H), 1.72 (m, 2H), 2.01 (m, 1H), 2.23 (m, 1H), 3.22 (m, 1H), 3.65 (m, 2H), 5.99 (br s, 1H).

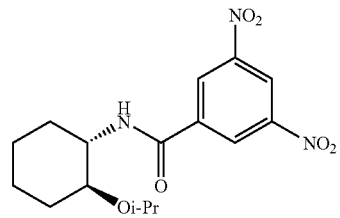

N-(2-Isopropoxy-cyclohexyl)-3,5-bis-trifluoromethyl-benzamide To a flame-dried test tube was added 7-(3,5-Bis-trifluoromethylbenzoyl)-7-azabicyclo[3.1.0]heptane (0.051 g, 0.15 mmol) and phenylphosphinic acid (4.3 mg, 20 mol %). The air was removed and replaced with argon. Isopropanol (60 µL, 0.9 mmol) was added via syringe to the test-tube followed by dichloromethane (0.55 mL). The reaction was stirred at ambient temperature for 24 h. The reaction was diluted with CH$_2$Cl$_2$, concentrated on silica gel, and purified by flash column chromatography with 6:1 hexanes/EtOAc. Recovered white solid (0.024 g, 39%). $^1$H NMR (400 MHz, CDCl$_3$): δ 1.16 (m, 6H), 1.37 (m, 4H), 1.64 (m, 1H), 1.68 (m, 1H), 2.13 (m, 1H), 2.29 (m, 1H), 3.23 (m, 1H), 3.62 (m, 2H), 6.19 (brs, 1H), 7.99 (s, 1H), 8.18 (s, 2H).

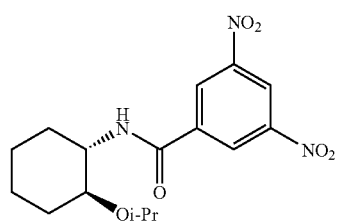

N-(2-Isopropoxy-cyclohexyl)-3,5-dinitro-benzamide To a flame-dried test tube was added (7-Aza-bicyclo[4.1.0]hept-7-yl)-(3,5-dinitro-phenyl)-methanone (0.043 g, 0.15 mmol) and phenylphosphinic acid (4.3 mg, 20 mol %). The air was removed and replaced with argon. isopropanol (60 µL, 0.9 mmol) was added via syringe to the test-tube followed by dichloromethane (0.5 mL). The reaction was stirred at ambient temperature for 24 h. The reaction was diluted with CH$_2$Cl$_2$, concentrated on silica gel, and purified by flash column chromatography with 6:1 hexanes/EtOAc. Recovered white solid (0.02 g, 39%). $^1$H NMR (250 MHz, CDCl$_3$): δ 1.10 (d, 6H), 1.29 (m, 4H), 1.65 (m, 2H), 2.03 (m, 1H), 2.32 (m, 1H), 2.23 (m, 1H), 3.67 (m, 2H), 6.31 (br s, 1H), 8.81 (s, 2H), 9.09 (s, 1H).

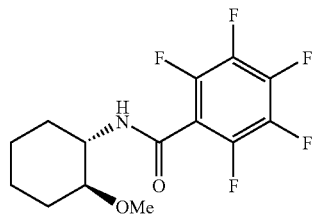

N-(2-Isopropoxy-cyclohexyl)-3,5-dinitro-benzamide To a flame-dried test tube was added (7-Aza-bicyclo[4.1.0]hept-7-yl)-(3,5-dinitro-phenyl)-methanone (0.043 g, 0.15 mmol) and BINOL phosphoric acid (5.0 mg, 10 mol %). The air was removed and replaced with argon. isopropanol (60 µL, 0.9 mmol) was added via syringe to the test-tube followed by dichloromethane (0.5 mL). The reaction was stirred at ambient temperature for 24 h. The reaction was diluted with CH$_2$Cl$_2$, concentrated on silica gel, and purified by flash column chromatography with 6:1 hexanes/EtOAc. Recovered white solid (0.012 g, 23%). $^1$H NMR (250 MHz, CDCl$_3$): δ 1.10 (d, 6H), 1.29 (m, 4H), 1.65 (m, 2H), 2.03 (m, 1H), 2.32 (m, 1H), 2.23 (m, 1H), 3.67 (m, 2H), 6.31 (br s, 1H), 8.81 (s, 2H), 9.09 (s, 1H). HPLC analysis: Chiralcel AD-H (hexane/iPrOH=90:10, 1.0 mL/min), t$_{r\text{-}major}$ 12.51 min, t$_{r\text{-}minor}$ 13.17 min (8% ee).

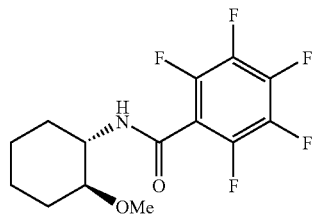

2,3,4,5,6-Pentafluoro-N-(2-methoxy-cyclohexyl)-benzamide To a flame-dried test tube was added (7-Aza-bicyclo[4.1.0]hept-7-yl)-pentafluorophenyl-methanone (0.044 g, 0.15 mmol) and phenylphosphinic acid (11 mg, 50 mol %). The air was removed and replaced with argon. Methyl alcohol (36 µL, 0.9 mmol) was added via syringe to the test-tube followed by dichloromethane (0.5 mL). The reaction was stirred at ambient temperature for 24 h. The reaction was diluted with CH$_2$Cl$_2$, concentrated on silica gel, and purified by flash column chromatography with 6:1 hexanes/EtOAc. Recovered white solid (0.041 g, 89%). $^1$H NMR (250 MHz, CDCl$_3$): δ 1.23 (m, 4H), 1.71 (m, 2H), 2.18 (m, 2H), 3.17 (m, 1H), 3.31 (s, 3H), 3.82 (m, 1H), 6.06 (brs, 1H).

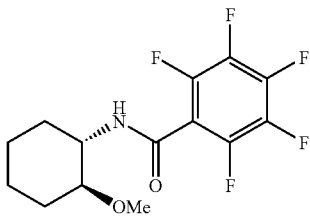

2,3,4,5,6-Pentafluoro-N-(2-methoxy-cyclohexyl)-benzamide To a flame-dried test tube was added (7-Aza-bicyclo[4.1.0]hept-7-yl)-pentafluorophenyl-methanone (0.029 g, 0.10 mmol) and (R) BINOL phosphoric acid (4.0 mg, 10 mol %). The air was removed and replaced with argon. Methyl alcohol (24 µL, 0.6 mmol) was added via syringe to the test-tube followed by dichloromethane (0.25 mL). The reaction was stirred at ambient temperature for 24 h. The reaction was diluted with $CH_2Cl_2$, concentrated on silica gel, and purified by flash column chromatography with 6:1 hexanes/EtOAc. Recovered white solid (0.026 g, 84%). $^1$H NMR (250 MHz, $CDCl_3$): δ 1.23 (m, 4H), 1.71 (m, 2H), 2.18 (m, 2H), 3.17 (m, 1H), 3.31 (s, 3H), 3.82 (m, 1H), 6.06 (brs, 1H).

HPLC analysis: Chiralcel AS-H (hexane/iPrOH=90:10, 1.0 mL/min), $t_{r-major}$ 7.85 min, $t_{r-minor}$ 16.88 min (2% ee).

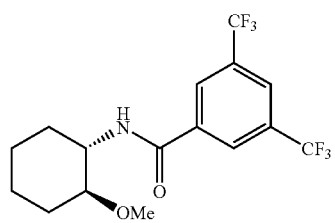

N-(2-Methoxy-cyclohexyl)-3,5-bis-trifluoromethyl-benzamide To a flame-dried test tube was added 7-(3,5-Bis-trifluoromethylbenzoyl)-7-azabicyclo[3.1.0]heptane (0.051 g, 0.15 mmol) and phenylphosphinic acid (11 mg, 50 mol %). The air was removed and replaced with argon. Methyl alcohol (12 mL, 0.3 mmol) was added via syringe to the test-tube followed by dichloromethane (0.5 mL). The reaction was stirred at ambient temperature for 24 h. The reaction was diluted with $CH_2Cl_2$, concentrated on silica gel, and purified by flash column chromatography with 6:1 hexanes/EtOAc. Recovered white solid (0.027 g, 49%). $^1$H NMR (250 MHz, $CDCl_3$): δ 1.22 (m, 4H), 1.64 (m, 2H), 2.11 (m, 2H), 3.17 (m, 1H), 3.29 (s, 3H), 3.79 (m, 1H), 6.37 (s, 1H), 7.91 (s, 1H), 8.09 (s, 2H).

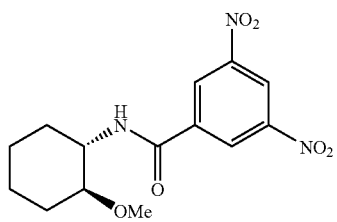

N-(2-Methoxy-cyclohexyl)-3,5-dinitro-benzamide To a flame-dried test tube was added (7-Aza-bicyclo[4.1.0]hept-7-yl)-(3,5-dinitro-phenyl)-methanone (0.0.44 g, 0.15 mmol) and phenylphosphinic acid (11 mg, 50 mol %). The air was removed and replaced with argon. Methyl alcohol (36 µL, 0.9 mmol) was added via syringe to the test-tube followed by dichloromethane (0.25 mL). The reaction was stirred at ambient temperature for 24 h. The reaction was diluted with $CH_2Cl_2$, concentrated on silica gel, and purified by flash column chromatography with 6:1 hexanes/EtOAc. Recovered white solid (0.031 g, 66%). $^1$H NMR (250 MHz, $CDCl_3$): δ 1.28 (m, 4H), 1.78 (m, 2H), 2.21 (m, 2H), 3.14 (m, 1H), 3.28 (s, 3H), 3.81 (m, 1H), 6.63 (d, 1H), 8.89 (s, 2H), 9.05 (s, 1H).

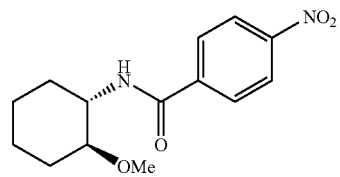

N-(2-Methoxy-cyclohexyl)-4-nitro-benzamide To a flame-dried test tube was added (7-Aza-bicyclo[4.1.0]hept-7-yl)-(4-nitro-phenyl)-methanone (0.036 g, 0.15 mmol) and phenylphosphinic acid (11.0 mg, 50 mol %). The air was removed and replaced with argon. Methyl alcohol (36 µL, 0.9 mmol) was added via syringe to the test-tube followed by dichloromethane (0.5 mL). The reaction was stirred at ambient temperature for 24 h. The reaction was diluted with $CH_2Cl_2$, concentrated on silica gel, and purified by flash column chromatography with 6:1 hexanes/EtOAc. Recovered white solid (0.029 g, 71%). $^1$H NMR (250 MHz, $CDCl_3$): δ 1.23 (m, 4H), 1.71 (m, 2H), 2.09 (m, 1H), 2.24 (m, 1H), 3.11 (m, 1H), 3.29 (m, 3H), 3.82 (m, 1H), 6.24 (br s, 1H), 7.84 (d, 2H), 8.19 (d, 2H).

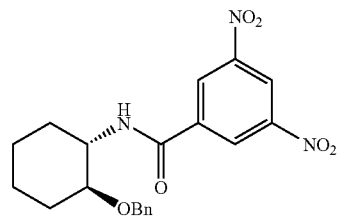

N-(2-Benzyloxy-cyclohexyl)-3,5-dinitro-benzamide To a flame-dried test tube was added (7-Aza-bicyclo[4.1.0]hept-7-yl)-(3,5-dinitro-phenyl)-methanone (0.044 g, 0.15 mmol) and (S)-3,3'-Bis(triphenylsilyl)-1,1'-binaphthyl-2,2'-diyl hydrogenphosphate (13.0 mg, 10 mol %). The air was removed and replaced with argon. Benzyl alcohol (30 µL, 0.9 mmol) was added via syringe to the test-tube followed by dichloromethane (0.5 mL). The reaction was stirred at ambient temperature for 24 h. The reaction was diluted with $CH_2Cl_2$, concentrated on silica gel, and purified by flash column chromatography with 6:1 hexanes/EtOAc. Recovered white solid (0.032 g, 53%). $^1$H NMR (400 MHz, $CDCl_3$): δ 1.24-1.86 (m, 6H), 2.29 (m, 2H), 3.31 (m, 1H), 3.89 (m, 1H), 4.39 (m, 1H), 4.71 (m, 1H), 6.06 (br s, 1H), 7.24 (m, 5H), 8.75 (s, 2H), 9.12 (s, 1H).

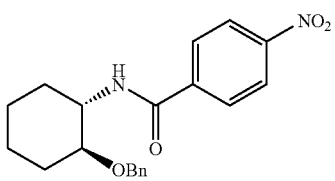

N-(2-Benzyloxy-cyclohexyl)-4-nitro-benzamide To a flame-dried test tube was added (7-Aza-bicyclo[4.1.0]hept-7-yl)-(4-nitro-phenyl)-methanone (0.024 g, 0.1 mmol) and phenylphosphinic acid (4.0 mg, 40 mol %). The air was removed and replaced with argon. Benzyl alcohol (68 μL, 0.6 mmol) was added via syringe to the test-tube followed by dichloromethane (0.25 mL). The reaction was stirred at ambient temperature for 24 h. The reaction was diluted with $CH_2Cl_2$, concentrated on silica gel, and purified by flash column chromatography with 6:1 hexanes/EtOAc. Recovered white solid (0.030 g, 95%). $^1$H NMR (400 MHz, $CDCl_3$): δ 1.09-1.84 (m, 6H), 2.21-2.35 (m, 2H), 3.29 (m, 1H), 3.88 (m, 1H), 4.38 (d, J=12.4 Hz, 1H), 4.68 (d, J=12.4 Hz, 1H), 5.96 (s, 1H), 7.24 (m, 5H), 7.72 (d, J=8.8 Hz, 2H), 8.21 (d, J=8.8 Hz, 2H).

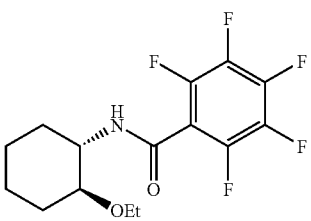

N-(2-Ethoxy-cyclohexyl)-2,3,4,5,6-pentafluoro-benzamide To a flame-dried test tube was added (7-Aza-bicyclo[4.1.0]hept-7-yl)-pentafluorophenyl-methanone (0.044 g, 0.15 mmol) and (S)-VAPOL phosphoric acid (9 mg, 10 mol %). The air was removed and replaced with argon. Trimethylsilyl ethoxide (47 μL, 0.3 mmol) was added via syringe to the test-tube followed by dichloromethane (0.25 mL). The reaction was stirred at ambient temperature for 24 h. The reaction was diluted with $CH_2Cl_2$, concentrated on silica gel, and purified by flash column chromatography with 6:1 hexanes/EtOAc. Recovered white solid (0.011 g, 21%). $^1$H NMR (250 MHz, $CDCl_3$): δ 0.96-1.78 (m, 6H), 1.99-2.89 (m, 2H), 3.22 (m, 2H), 3.53 (m, 2H), 3.79 (m, 2H), 5.83 (s, 1H).

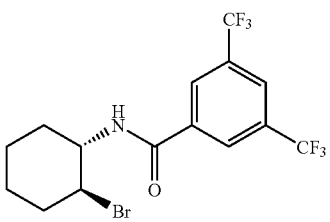

N-(2-Bromo-cyclohexyl)-3,5-bis-trifluoromethyl-benzamide To a flame-dried test tube was added 7-(3,5-Bis-trifluoromethylbenzoyl)-7-azabicyclo[3.1.0]heptane (0.051 g, 0.15 mmol) and (R)-VAPOL phosphoric acid (9 mg, 10 mol %). The air was removed and replaced with argon. Bromotrimethylsilane 30 μL, 0.23 mmol) was added via syringe to the test-tube followed by dichloromethane (1.0 mL). The reaction was stirred at −78° C. for 24 h. The reaction was diluted with $CH_2Cl_2$, concentrated on silica gel, and purified by flash column chromatography with 6:1 hexanes/EtOAc. Recovered white solid (0.070 g, 91%). $^1$H NMR (400 MHz, $CDCl_3$): δ 1.33 (m, 3H), 1.72 (m, 2H), 1.97 (m, 1H), 2.21 (m, 1H), 2.40 (m, 1H), 3.99 (m, 1H), 4.21 (m, 1H), 6.81 (br s, 1H), 7.92 (s, 1H), 8.19 (s, 2H). HPLC analysis: Chiralcel AS-H (hexane/iPrOH=90:10, 1.0 mL/min), $t_{r-major}$ 7.77 min, $t_{r-minor}$ 5.75 min (5% ee).

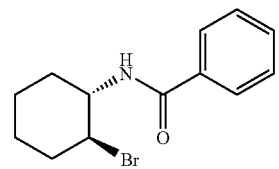

N-(2-Bromo-cyclohexyl)-benzamide To a flame-dried test tube was added 7-aza-bicyclo[4.1.0]hept-7-yl)-phenyl-methanone (0.020 g, 0.1 mmol) and (R)—PA-1 (6 mg, 10 mol %). The air was removed and replaced with argon. Bromotrimethylsilane (14 μL, 0.11 mmol) was added via syringe to the test-tube followed by dichloromethane (1 mL). The reaction was stirred at −78° C. for 24 h. The reaction was diluted with $CH_2Cl_2$, concentrated on silica gel, and purified by flash column chromatography with 6:1 hexanes/EtOAc. Recovered white solid (0.025 g, 91% yield). $^1$H NMR (250 MHz, $CDCl_3$): δ 1.13-1.98 (m, 6H), 2.32 (m, 2H), 4.01 (m, 2H), 6.09 (s, 1H), 7.38 (m, 3H), 8.71 (m, 2H).

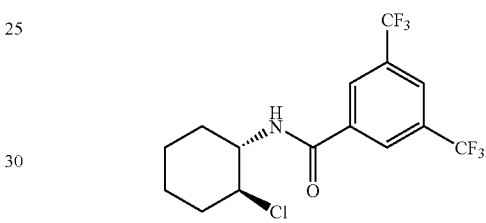

N-(2-Chloro-cyclohexyl)-3,5-bis-trifluoromethyl-benzamide To a flame-dried test tube was added 7-(3,5-Bis-trifluoromethylbenzoyl)-7-azabicyclo[3.1.0]heptane (0.067 g, 0.2 mmol) and (R)-VAPOL phosphoric acid (12 mg, 10 mol %). The air was removed and replaced with argon. Chlorotrimethylsilane (16 μL, 0.125 mmol) was added via syringe to the test-tube followed by dichloromethane (0.25 mL). The reaction was stirred at ambient temperature for 24 h. The reaction was diluted with $CH_2Cl_2$, concentrated on silica gel, and purified by flash column chromatography with 6:1 hexanes/EtOAc. Recovered white solid (0.043 g, 93%). $^1$H NMR (250 MHz, $CDCl_3$): δ 1.41 (m, 3H), 1.69 (m, 3H), 2.17 (m, 2H), 3.75 (m, 1H), 3.99 (m, 1H), 6.73 (br s, 1H), 7.85 (s, 1H), 8.15 (s, 2H). HPLC analysis: Chiralcel AS-H (hexane/iPrOH=90:10, 1.0 mL/min), $t_{r-major}$ 7.73 min, $t_{r-minor}$ 5.91 min (9% ee).

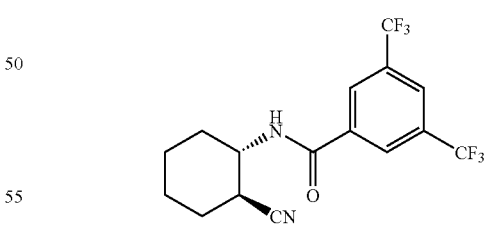

N-(2-Cyano-cyclohexyl)-3,5-bis-trifluoromethyl-benzamide To a flame-dried test tube was added 7-(3,5-Bis-trifluoromethylbenzoyl)-7-azabicyclo[3.1.0]heptane (0.051 g, 0.38 mmol) and (R)-VAPOL phosphoric acid (9 mg, 10 mol %). The air was removed and replaced with argon. Trimethylsilyl cyanide (80 μL, 0.60 mmol) was added via syringe to the test-tube followed by 1,2-dichloroethane (0.5 mL). The reaction was stirred at ambient temperature for 24 h. The reaction was diluted with $CH_2Cl_2$, concentrated on silica gel, and purified by flash column chromatography with 6:1 hexanes/EtOAc. Recovered white solid (0.0334 g, 61%). $^1$H NMR (250 MHz, CDCl$_3$): δ 1.23-2.21 (m, 6H), 2.69 (m, 2H), 4.11 (m, 2H), 6.38 (s, 1H), 7.91 (s, 1H), 8.24 (s, 1H). HPLC analysis: Chiralcel AS-H (hexane/iPrOH=90:10, 1.0 mL/min), t$_{r-major}$ 6.09 min, t$_{r-minor}$ 7.44 min (8% ee).

Procedure for the Preparation of Aziridine Substrates

Aziridines 7-aza-bicyclo[4.1.0]heptane-7-carboxylic acid benzyl ester, 7-aza-bicyclo[4.1.0]heptane-7-carboxylic acid tert-butyl ester, and (7-Aza-bicyclo[4.1.0]hept-7-yl)-(4-nitro-phenyl)-methanone were prepared by literature procedure.[2]

Aziridines (7-Aza-bicyclo[4.1.0]hept-7-yl)-(3,5-dinitrophenyl)-methanone, 7-(3,5-Bis-trifluoromethylbenzoyl)-7-azabicyclo[3.1.0]heptane, 7-(3,5-Bis-trifluoromethylbenzoyl)-7-azabicyclo[4.1.0]hept-3-ene, 8-(3,5-Bis-trifluoromethylbenzoyl)-8-azbicyclo[5.1.0]octane, N-(3,5-Bis-trifluoromethylbenzoyl)-2,3-iminotetralin, and cis-1-(3,5-Bis-trifluoromethylbenzoyl)-2,3-dimethylaziridine, were prepared by the literature procedure.[3]

6-(3,5-Bis-trifluoromethylbenzoyl)-6-azabicyclo[3.1.0] hexane was prepared by the following modified procedure of the reported method.[3,4]

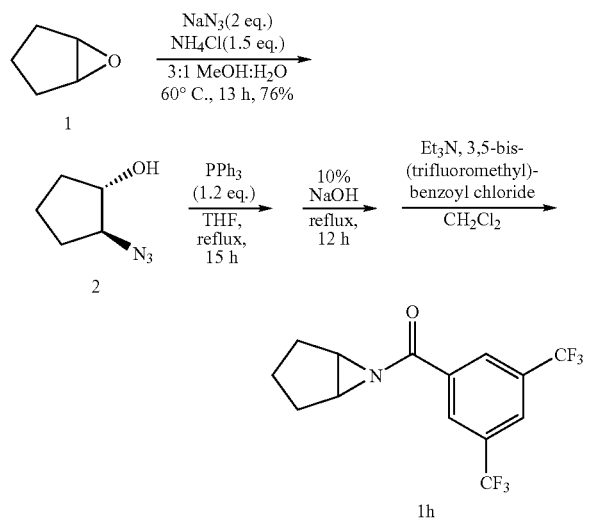

To a solution of 3:1 MeOH:H$_2$O (300 mL) was added cyclopentene oxide (1)(13 mL, 149.0 mmol), followed by the addition of NaN$_3$ (19.4 g, 298.0 mmol) and NH$_4$Cl (12.4 g, 223.5 mmol). The mixture was heated at 60° C. for 13 h. Most of the MeOH was evaporated in vacuo and then extracted three times with CH$_2$Cl$_2$, washed with brine, dried over Na$_2$SO$_4$ and concentrated to afford 2 as a tan oil (17.7 g, 94%).

Azido alcohol 2 (5.0 g, 39.3 mmol) was added to a flame-dried flask. The air was removed and replaced with argon. Anhydrous THF (40.0 mL) was added followed by PPh$_3$ (12.3 g, 47.0 mmol) and heated under reflux for 15 h. Most of the THF was removed in vacuo at ambient temperature. Added 10% NaOH (50 mL) and refluxed for 12 h then extracted three times each with ether then CH$_2$Cl$_2$, washed with brine, dried over MgSO$_4$ and concentrated at ambient temperature leaving about 100 mL CH$_2$Cl$_2$. Benzoylation was completed in CH$_2$Cl$_2$ following the reported literature procedure.[3] Calculations for the benzoylation were based on using 18.1 mmol 3,5-bis-(trifluoromethyl)-benzoyl chloride.

cis-1-(3,5-Bis-trifluoromethylbenzoyl)-2,3-diphenylaziridine was prepared by the following modified procedure of the reported method.[3,5]

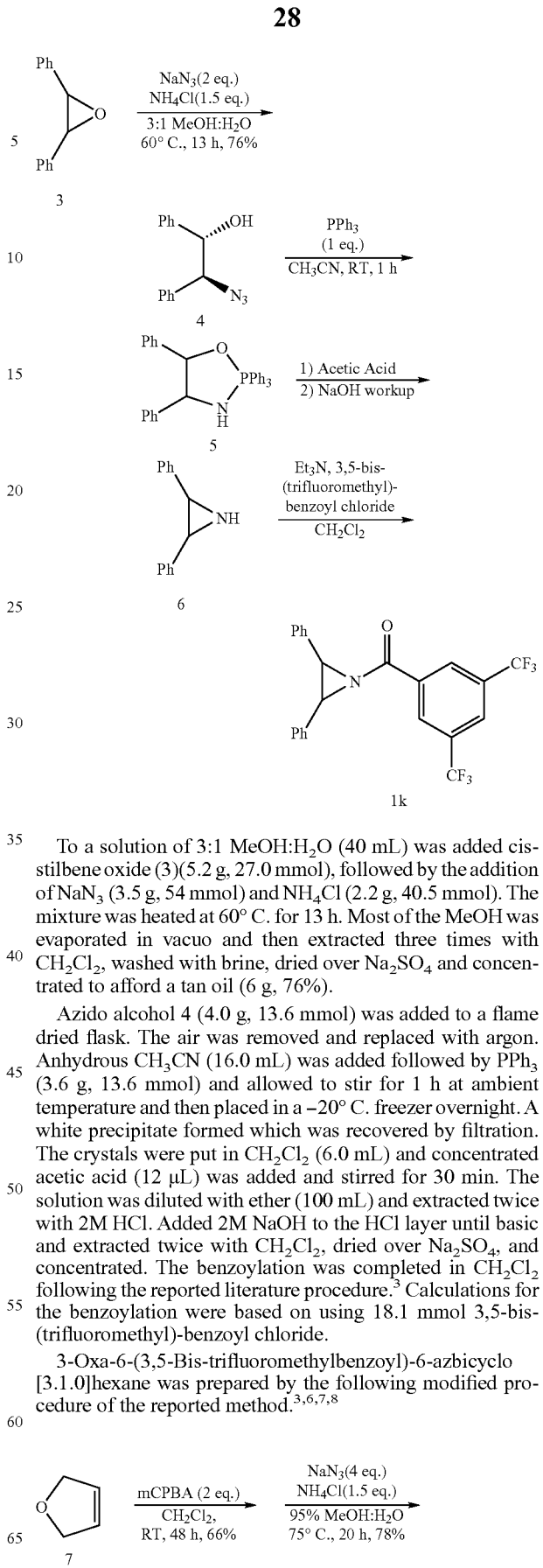

To a solution of 3:1 MeOH:H$_2$O (40 mL) was added cis-stilbene oxide (3)(5.2 g, 27.0 mmol), followed by the addition of NaN$_3$ (3.5 g, 54 mmol) and NH$_4$Cl (2.2 g, 40.5 mmol). The mixture was heated at 60° C. for 13 h. Most of the MeOH was evaporated in vacuo and then extracted three times with CH$_2$Cl$_2$, washed with brine, dried over Na$_2$SO$_4$ and concentrated to afford a tan oil (6 g, 76%).

Azido alcohol 4 (4.0 g, 13.6 mmol) was added to a flame dried flask. The air was removed and replaced with argon. Anhydrous CH$_3$CN (16.0 mL) was added followed by PPh$_3$ (3.6 g, 13.6 mmol) and allowed to stir for 1 h at ambient temperature and then placed in a −20° C. freezer overnight. A white precipitate formed which was recovered by filtration. The crystals were put in CH$_2$Cl$_2$ (6.0 mL) and concentrated acetic acid (12 μL) was added and stirred for 30 min. The solution was diluted with ether (100 mL) and extracted twice with 2M HCl. Added 2M NaOH to the HCl layer until basic and extracted twice with CH$_2$Cl$_2$, dried over Na$_2$SO$_4$, and concentrated. The benzoylation was completed in CH$_2$Cl$_2$ following the reported literature procedure.[3] Calculations for the benzoylation were based on using 18.1 mmol 3,5-bis-(trifluoromethyl)-benzoyl chloride.

3-Oxa-6-(3,5-Bis-trifluoromethylbenzoyl)-6-azbicyclo [3.1.0]hexane was prepared by the following modified procedure of the reported method.[3,6,7,8]

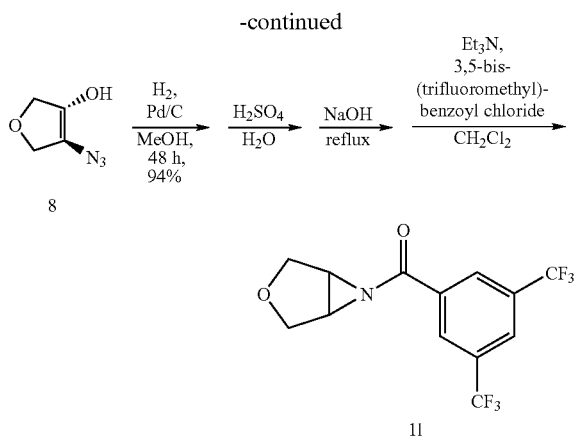

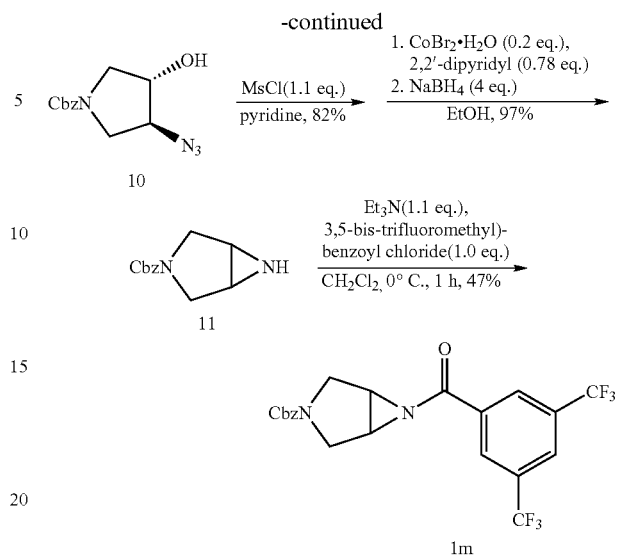

2,4-Dihydrofuran (7)(5.3 mL, 71.3 mmol) was added to a 500 mL round bottom flask containing CH$_2$Cl$_2$ (250 mL). mCPBA was added and the solution stirred at ambient temperature for two days. The solution was washed twice with aqueous Na$_2$S$_2$O$_3$, then sat. Na$_2$CO$_3$ and dried over Na$_2$SO$_4$. The organic layer was then concentrated to afford the epoxide as a colorless oil (3.7 g, 66%).

NaN$_3$ (11.2 g, 172 mmol) and NH$_4$Cl (3.6 g, 64.5 mmol) were added to 80 mL 95% MeOH in H$_2$O and stirred until most dissolved. The above epoxide (3.7 g, 43 mmol) was added and the solution was heated at 75° C. for 20 h. It was then cooled to room temperature and filtered to remove excess NaN$_3$. The filtrate was diluted with water and extracted four times with EtOAc, dried over Na$_2$SO$_4$, and concentrated to afford azido alcohol 8 as a tan oil (4.3 g, 78%)

To a flame dried 100 mL round bottom flask under argon was added 10% Pd/C (304 mg) followed by MeOH (15 mL) while stirring. Added azido alcohol 8 via syringe and stirred under an atmosphere of hydrogen for 48 h. Reaction was monitored by TLC until completion and filtered over a pad of celite and concentrated to afford the amino alcohol a tan solid (1.5 g, 94%)

The amino alcohol (1.5 g, 14.5 mmol) was added to a 100 mL round bottom flask. Approximately 4 mL H$_2$O was added and the mixture cooled to 0° C. Concentrated H$_2$SO$_4$ (0.78 mL) in H$_2$O (1.8 mL) was added dropwise and the mixture stirred at 0° C. for 1 h. The H$_2$O was removed by distillation and continued heating at 10° C. for 1 h. Added 20% NaOH and heated at 100° C. overnight. The solution was cooled to room temperature and extracted four times with CH$_2$Cl$_2$ and dried over Na$_2$SO$_4$. Most of the solvent was removed carefully in vacuo (the resulting aziridine is volatile). The benzoylation was completed in CH$_2$Cl$_2$ following the reported literature procedure.[3] Calculations for the benzoylation were based on using 18.1 mmol 3,5-bis-(trifluoromethyl)-benzoyl chloride.

3-Carbobenzyloxy-6-(3,5-Bis-trifluoromethylbenzoyl)-3, 6-diazbicyclo[3.1.0]hexane was prepared by the following modified procedure of the reported method.[3,9]

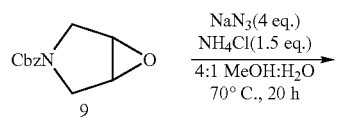

To a solution of 4:1 MeOH:H$_2$O was added epoxide 9 (4.8 g, 22.0 mmol) followed by the addition of NaN$_3$ (2.86 g, 44.0 mmol) and NH$_4$Cl (1.8 g, 33.0 mmol) while stirring. The mixture was heated at 70° C. for 20 h and then diluted with H$_2$O, extracted three times with CH$_2$Cl$_2$ and dried over Na$_2$SO$_4$. The organic layer was concentrated to afford a red oil, which was carried on to the next step. The air was removed from the flask and replaced with argon. Pyridine (13.0 mL) was added and cooled to 0° C. Methanesulfonyl chloride (1.9 mL, 24.2 mmol) was added slowly dropwise via syringe. The solution was allowed to warm to ambient temperature and stirred for 20 h. The reaction mixture was poured over ice cold H$_2$O and extracted with CH$_2$Cl$_2$ twice and then washed with two 50 mL portions of 1M HCl followed by brine. The organic phase was concentrated to afford a red oil (6.1 g, 82%), which was diluted with EtOH (60 mL) and added to a 500 mL flask containing a 0° C. solution of CoBr$_2$.H$_2$O (0.92 g, 4 mmol) and 2,2'-dipyridyl (2.2 g, 14 mmol) in 300 mL absolute EtOH. Sodium borohydride (3.1 g, 82.0 mmol) was added very slowly in small portions over 1 h while keeping at 0° C. The mixture was allowed to slowly warm to ambient temperature and stirred for an additional 2 h. The mixture was then slowly poured over H$_2$O (1000 mL) and extracted three times with CH$_2$Cl$_2$, dried over Na$_2$SO$_4$ and concentrated to afford a brown oil which was purified by flash column chromatography with CH$_2$Cl$_2$ and MeOH. Recovered 3.77 g, 97% of aziridine 11.

Aziridine 11 (2.0 g, 9.2 mmol) was added to an oven dried flask. The air was removed and replaced with argon. CH$_2$Cl$_2$ (20 mL) was added followed by Et$_3$N (1.4 mL, 10.1 mmol) and cooled to 0° C. A bubbler was attached to the flask and 3,5-Bis-(trifluoromethyl)benzoylchloride (1.64 mL, 9.2 mmol) in CH$_2$Cl$_2$ (6.0 mL) was added slowly dropwise. The Solution was stirred at 0° C. for 1 h. H$_2$O (20 mL) was added and let warm to ambient temperature and extracted three times with CH$_2$Cl$_2$, washed with brine, dried over Na$_2$SO$_4$, concentrated and purified by flash column chromatography with 6:1 hexanes:acetone to afford a 1 m as a colorless oil (1.8 g, 47%).

REFERENCES

1) Bao, J.; Wulff, W.; Dominy, J.; Fumo, M. J.; Grant, E. B.; Rob, A. C.; Whitcomb, M. C.; Yeung, S.-M.; Ostrander, R. L.; Rheingold, A. L. *J. Am. Chem. Soc.* 1996, 118, 3392.

2a) Ekegren, J. K.; Roth, P.; Kallstrom, K.; Tarnai, T.; Andersson, P. G. *Org. Biomol. Chem.* 2003, 1, 358. b) Mordini, A.; Russo, F.; Valacchi, M.; Zani, L.; Degl'Innocenti, A.; Reginato, G. *Tetrahedron*. 2002, 58, 7153. c) Hayashi, M.; Ono, K.; Hoshimi, H.; Oguni, N. *Tetrahedron*. 1996, 52, 7817.

3) Fukuta, Y.; Mita, T.; Fukuda, N.; Kanai, M.; Shibasaki, M. *J. Am. Chem. Soc.* 2006, 128, 6312.

4) Zhang, Z.; Scheffold, R. *Helv. Chem. Acta.* 1993, 76, 2602.

5) Pöchlauer, P.; Müller, E. P.; Peringer, P. *Helv. Chem. Acta.* 1984, 67, 1238.

6) Anderson, W. K.; Milowsky, A. S. *J. Med. Chem.* 1986, 29, 2241.

7) Marquis, R. W.; ru, Y.; Zeng, J.; Trout, R. E. L.; LoCastro, S. M.; Gribble, A. D.; Witherington, J.; Fenwick, A. E.; Garnier, B.; Tomaszek, T.; Tew, D.; Hemling, M. E.; Quinn, k C. J.; Smith, W. W.; Zhao, B.; McQueney, M. S.; Janson, C. A.; D'Alessio, K.; Veber, D. F. *J. Med. Chem.*, 2001, 44, 725.

8) Fanta, P. E.; Walsh, E. N. *J. Org. Chem.* 1966, 31, 59.

9) Oida, S.; Kuwano, H.; Ohashi, Y.; Ohki, E. *Chem. Pharm. Bull.* 1970, 18, 2478.

Example 2

Preliminary Studies—Brønsted Acid-Catalyzed Ring-Opening of Aziridines: The catalytic asymmetric ring-opening of aziridines is an important, actively pursued area of research. Chiral Phosphoric Acid Catalysts can be seen in Table 1. The method of the current invention involves catalyzation of the ring-opening of meso-aziridines by the chiral Brønsted acids with azide to provide a 1,2-diamine precursors in high enantiomeric excess (see Table 2). These desymmetrization reactions occur at room temperature and with very high yield. Chiral 1,2-diamines have an important value synthetically and this methodology is the first example of a chiral Brønsted acid catalyzing such ring-opening type reaction with high selectivity. PA5 has been shown to be an excellent catalyst in the limited study so far. Development of a method for the kinetic resolution of aziridines using PA5 is also foreseen.

A general procedure for the catalytic asymmetric ring opening of meso aziridines: The aziridine (1.5 equiv) and chiral Brønsted acid (10 mol %) were weighed into a flame-dried, screw-cap test tube with septa and stir bar. The test tube was evacuated and back-filled with argon and repeated three times. To the mixture was added azidotrimethylsilane (1 equiv) drop-wise followed by immediate addition of 0.5 mL of dry 1,2-dichloroethane via syringe. The mixture was stirred vigorously for the desired reaction time as monitored by TLC for product formation. Dichloromethane (4-5 mL) and a scoop of silica gel were added and the solvent removed by rotary evaporation to give a crude mixture adhered to silica that was purified by column chromatography to provide the desired product.

TABLE 1

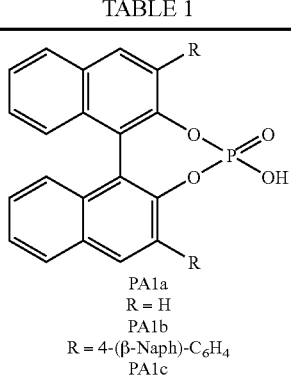

PA1a R = H
PA1b R = 4-(β-Naph)-C$_6$H$_4$
PA1c

TABLE 1-continued

R = 4-(α-Naph)-C$_6$H$_4$
PA1d
R = β-Naph

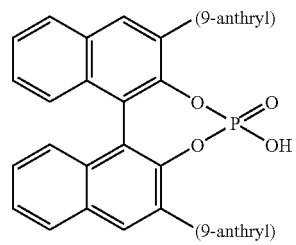

PA2

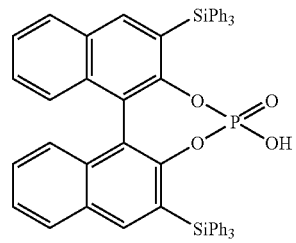

PA3

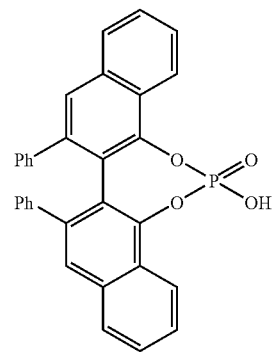

PA4

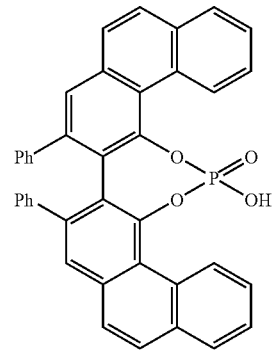

PA5

TABLE 2

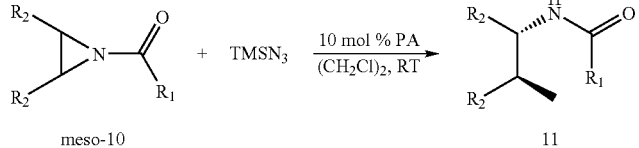

| entry | R₁ | R₂ | time, h | PA | yield, %ᵃ | ee | entry | R₁ | R₂ | time, h | PA | yield, %ᵃ | ee |
|---|---|---|---|---|---|---|---|---|---|---|---|---|---|
| 1 | O-t-Bu | —(CH₂)₄— | 30 | PA5 | 48 | 0 | 1 | 3,5-CF₃C₆H₃ | —(CH₂)₄— | 21 | PA5 | 94 | 96 |
| 2 | OBn | —(CH₂)₄— | 22 | PA5 | 49 | 0 | 2 | 3,5-CF₃C₆H₃ | —(CH₂)₄— | 21 | PA4 | 90 | 94 |
| 3 | 3,5-NO₂C₆H₃ | —(CH₂)₄— | 6 | PA5 | 90 | 77 | 3 | 3,5-CF₃C₆H₃ | —CH₂CH=CHCH₂— | 21 | PA5 | 84 | 92 |
| 4 | 3,5-NO₂C₆H₃ | —(CH₂)₄— | 46 | PA3 | 90 | 0 | 4 | 3,5-CF₃C₆H₃ | Me | 21 | PA5 | 88 | 86 |
| 5 | C₆F₅ | —(CH₂)₄— | 21 | PA5 | 58 | 12 | 5 | 3,5-CF₃C₆H₃ | CH₃(CH₂)₂— | 23 | PA5 | 33 | 58 |
| 6 | 3,5-CF₃C₆H₃ | 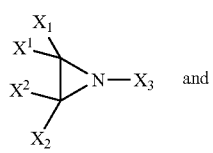 | 21 | PA5 | 78 | 71 | 6 | 3,5-CF₃C₆H₃ | —(CH₂)₅— | 23 | PA5 | 31 | 93 |
| 7 | 3,5-CF₃C₆H₃ | 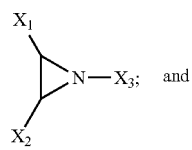 | 96 | PA5 | 90 | 70 | 7 | 3,5-CF₃C₆H₃ | —(CH₂)₅— | 91 | PA5 | 64 | 91 |
| 8 | 3,5-CF₃C₆H₃ | —CH₂OCH₂— | 48 | PA5 | 49 | 87 | 8 | 3,5-CF₃C₆H₃ | —(CH₂)₅— | 72 | PA5 | 95 | 69 @ 60° C. |
| 9 | 3,5-CF₃C₆H₃ | —C₆H₅— | 48 | PA5 | 95 | 83 | 9 | 3,5-CF₃C₆H₃ | —(CH₂)₃— | 55 | PA5 | 68 | 84 |
| 10 | 3,5-CF₃C₆H₃ | 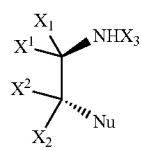 | 96 | PA5 | 96 | 67 | | | | | | | |

ᵃIsolated yields.

What is claimed is:

1. A process for the preparation of a nucleophilic addition product of an aziridine and a nucleophile, the process comprising treating the arizidine with the nucleophile in the presence of a biaryl phosphoric acid catalyst.

2. The process of claim 1 wherein the aziridine has the formula

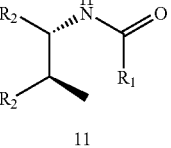

and the nucleophilic addition product has the formula

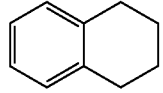

wherein

Nu is a nucleophile residue, $X_1$, $X^1$, $X_2$ and $X^2$ are independently hydrogen, hydrocarbyl, substituted hydrocarbyl, or heterocyclo, and, optionally, (i) $X_1$ and $X_2$ and the ring carbon atoms to which they are respectively bonded, in combination, form a fused ring system, (ii) $X_1$ and $X^1$ and the ring carbon atom to which they are bonded, in combination, form a spiro ring, or (ii) $X_2$ and $X^2$ and the ring carbon atom to which they are bonded, in combination, form a spiro ring, and $X_3$ is hydrocarbyl, substituted hydrocarbyl, heterocyclo, silyl, acyl or amine protecting group.

3. The process of claim 1 wherein the aziridine has the formula

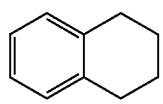

and the nucleophilic addition product has the formula

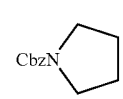

wherein

Nu is a nucleophile residue, $X_1$, and $X_2$ are independently hydrogen, hydrocarbyl, substituted hydrocarbyl, or heterocyclo, and, optionally, (i)

$X_1$ and $X_2$ and the ring carbon atoms to which they are respectively bonded, in combination, form a fused ring system, and $X_3$ is hydrocarbyl, substituted hydrocarbyl, heterocyclo, silyl, acyl or amine protecting group.

4. The process of claim 2 wherein the biaryl phosphoric acid catalyst has the formula

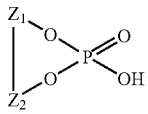

wherein $Z_1$ and $Z_2$ are aryl.

5. The process of claim 1 wherein the nucleophile is a silylazide and Nu is azide.

6. The process of claim 1 wherein the nucleophile is a trialkylsilylazide and Nu is —$N_3$.

7. The process of claim 1 wherein the nucleophile is an alcohol and Nu is —$OT_1$ wherein $T_1$ is hydrocarbyl, substituted hydrocarbyl or heterocyclo.

8. The process of claim 1 wherein the nucleophile is a cyanide and Nu is cyano.

9. The process of claim 1 wherein the nucleophile is a halonucleophile and Nu is chloro, bromo, fluoro or iodo.

10. The process of claim 2 wherein the nucleophile is a silylazide and Nu is azide.

11. The process of claim 2 wherein the nucleophile is a trialkylsilylazide and Nu is —$N_3$.

12. The process of claim 2 wherein the nucleophile is an alcohol and Nu is —$OT_1$ wherein $T_1$ is hydrocarbyl, substituted hydrocarbyl or heterocyclo.

13. The process of claim 2 wherein the nucleophile is a cyanide and Nu is cyano.

14. The process of claim 2 wherein the nucleophile is a halonucleophile and Nu is chloro, bromo, fluoro or iodo.

15. The process of claim 2 wherein $X_3$ is hydrocarbyl or acyl.

16. The process of claim 2 wherein $X_3$ is —C(O)A wherein A is hydrocarbyl, substituted hydrocarbyl, or heterocyclo.

17. The process of claim 3 wherein $X_3$ is —C(O)A wherein A is hydrocarbyl, substituted hydrocarbyl, or heterocyclo.

18. The process of claim 1 wherein the nucleophile is an amine, amide, azide, mercaptan, alcohol, alkoxide, thiolate, carbanion, cyanide, thiocyanate, acetate, formate or chloroformate, bisulfite, organocuprate, organozinc, organolithium, Grignard reagent, enolate, acetylide, or hydride.

19. The process of claim 1 wherein the aziridine is meso- in nature and the phosphoric acid catalyzes the addition of the nucleophile to provide an asymmetric nucleophilic addition product.

20. The process of claim 1 wherein the aziridine is racemic in nature and the phosphoric acid catalyzes a kinetic resolution of the racemic aziridine to provide a chiral nucleophilic addition product.

* * * * *